(12) United States Patent
Munroe et al.

(10) Patent No.: US 7,473,537 B1
(45) Date of Patent: Jan. 6, 2009

(54) CLONED GLUCAGON-LIKE PEPTIDE-2 RECEPTORS

(75) Inventors: Donald G. Munroe, Waterdown (CA); Ashwani K. Gupta, Mississauga (CA); Tejal B. Vyas, Mississauga (CA); Kirk McCallum, Mississauga (CA); Ermi Fan, Toronto (CA)

(73) Assignee: NPS Pharmaceuticals, Inc., Bedminster, NJ (US)

( * ) Notice: Subject to any disclaimer, the term of this patent is extended or adjusted under 35 U.S.C. 154(b) by 0 days.

(21) Appl. No.: 09/331,127

(22) PCT Filed: Dec. 15, 1997

(86) PCT No.: PCT/CA97/00969

§ 371 (c)(1),
(2), (4) Date: Oct. 19, 1999

(87) PCT Pub. No.: WO98/25955

PCT Pub. Date: Jun. 18, 1998

(51) Int. Cl.
*C12N 15/09* (2006.01)
*C12P 21/02* (2006.01)
*C12N 5/08* (2006.01)
*C07K 14/435* (2006.01)
*C07K 14/705* (2006.01)
*G01N 33/53* (2006.01)

(52) U.S. Cl. .................. 435/69.1; 435/70.1; 435/7.21; 435/320.1; 435/325; 536/23.5; 530/351

(58) Field of Classification Search ............... None
See application file for complete search history.

(56) References Cited

U.S. PATENT DOCUMENTS 5,494,806 A   2/1996   Segre et al. ............... 435/691
5,776,725 A   7/1998   Kindsvogel et al. ........ 435/69.1

OTHER PUBLICATIONS

MacNeil et al.; (1994); Biochem. Biophys. Res. Comm.; vol. 198; pp. 328-334.
Ishihara et al.; (1991); EMBO; vol. 10; pp. 1635-1641.
Drucker et al., "Induction of Intestinal Epithelial Proliferation By Glucagon-Like Peptide 2", Proc. Natl. Acad. Sci., Medical Sciences, vol. 93, pp. 7911-7916, Jul. 1996.
Cheeseman et al., "The Effect of GIP and Glucagon-Like Peptides On Intestinal Basolateral Membrane Hexose Transport", American Physiological Society, 1996, pp. G477-G482.

*Primary Examiner*—Christine J Saoud
*Assistant Examiner*—Fozia M Hamud
(74) *Attorney, Agent, or Firm*—Stoel Rives LLP

(57) ABSTRACT

The invention relates to nucleotides and amino acid sequences encoding glucagon-like peptide 2 receptors, recombinant host cells transformed with such nucleotides, and methods of using the same in drug screening and related applications.

15 Claims, 11 Drawing Sheets

Figure 3:
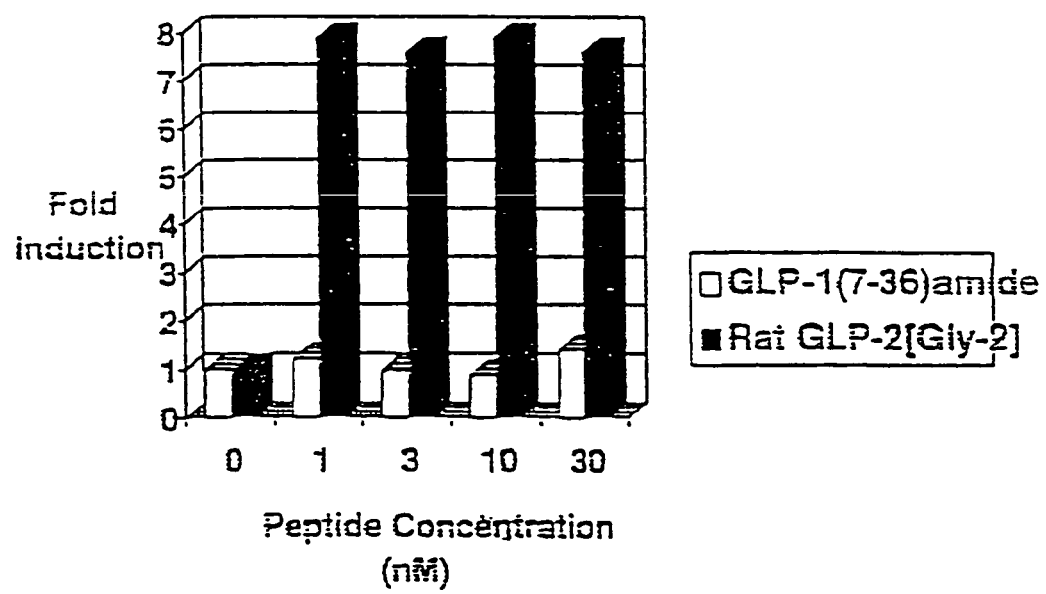

```
   1  AAGCTTCGCG  GCCTCTGCAG  AKGACTTGTG  CAAACACTTC  CTCTCTGGAC
  51  AAGGAGGAAT  GCAGGAGGCC  ACCGCCTGCA  GTACATCTTG  GAGTGTTGGA
 101  GGGATGTGCC  TGCACTTGTG  AACGGGCGCC  AGGAGAATGA  GGCCCCAACC
 151  AAGCCCGGCA  GTGCCCAGTA  GATGCAGAGA  GGCACCCGTG  CCCCGAGTGA
 201  GGGCACAGCC  AGTGGGCATC  CCTGAGGCCC  AGGGGCCCGT  TCCTCTCCAC
 251  TCCCAACAGA  TGCGTCTGCT  GTGGGGCCCT  GGGAGGCCCT  TCCTCGCCCT
 301  GCTTCTGCTG  GTTTCCATCA  AGCAAGTTAC  AGGATCGCTC  CTCAAGGAGA
 351  CAACTCAGAA  GTGGGCTAAT  TATAAGGAGA  AGTGTCTGGA  AGACTTGCAC
 401  AATAGACTTT  CTGGCATATT  TTGTAATGGG  ACATTTGATC  GGTATGTGTG
 451  CTGGCCTCAT  TCTTATCCTG  GAAATGTCTC  TGTTCCCTGT  CCTTCATACT
 501  TACCTTGGTG  GAATGCAGAG  AGCCCAGGAA  GGGCCTACAG  ACACTGCTTG
 551  GCTCAGGGGA  CTTGGCAGAC  GCGAGAGAAC  ACCACAGATA  TTTGGCAGGA
 601  TGAATCAGAA  TGCTCAGAGA  ACCACAGCTT  CAGACAAAAC  GTGGATCACT
 651  ACGCCTTGCT  ATACACCTTG  CAGCTGATGT  ACACTGTGGG  CTACTCCGTG
 701  TCTCTCATCT  CCCTCTTCTT  GGCTCTTACA  CTCTTCTTGT  TCCTTCGAAA
 751  ACTGCATTGC  ACACGCAATT  ACATCCACAT  GAACCTGTTC  GCTTCGTTCA
 801  TCCTGAAAGT  TCTGGCTGTC  CTGGTGAAGG  ACATGGTCTC  CCACAACTCT
 851  TACTCCAAGA  GGCCCGATGA  TGAGAGTGGA  TGGATGTCAT  ATCTGTCAGA
 901  GACATCCGTC  TCCTGTCGCT  CCGTCCAGGT  CCTCCTGCAC  TACTTTGTGG
 951  GCACCAATCA  CTTGTGGCTG  CTGGTTGAAG  GACTTTACCT  CCACACTCTG
1001  CTGGAGCCCA  CAGTGTTTCC  TGAAAGGCGG  CTGTGGCCCA  AGTACCTGGT
1051  GGTGGGTTGG  GCCTTCCCCA  TGCTGTTTGT  TATTCCCTGG  GGTTTTGCCC
1101  GTGCACACCT  GGAGAACACA  CGGTGCTGGG  CCACAAATGG  GAACCTGAAA
1151  ATCTGGTGGA  TCATCAGAGG  ACCCATGCTG  CTTTGTGTAA  CAGTTAATTT
1201  CTTCATCTTC  CTCAAGATTC  TCAAGCTTCT  CATTTCTAAG  CTCAAAGCTC
1251  ATCAGATGTG  CTTCAGAGAC  TACAAATACA  GATTGGCGAA  ATCAACGTTG
1301  CTCCTCATTC  CTTTGTTGGG  GGTTCATGAG  GTCCTCTTCA  CTTTCTTCCC
1351  CGACGACCAA  GTTCAAGGAT  TTTCAAAACG  TATTCGACTC  TTCATCCAGC
1401  TGACACTGAG  CTCTGTCCAC  GGATTTCTGG  TGGCCTTGCA  GTATGGCTTT
```

FIGURE 1

```
  1  MRPQPSPAVP  SRCREAPVPR  VRAQPVGIPE  AQGPVPLHSQ  QMRLLWGPGR

51  PFLALLLLVS  IKQVTGSLLK  ETTQKWANYK  EKCLEDLHNR  LSGIFCNGTF

101  DRYVCWPHSY  PGNVSVPCPS  YLPWWNAESP  GRAYRHCLAQ  GTWQTRENTT

151  DIWQDESECS  ENHSFRQNVD  HYALLYTLQL  MYTVGYSVSL  ISLFLALTLF

201  LFLRKLHCTR  NYIHMNLFAS  FILKVLAVLV  KDMVSHNSYS  KRPDDESGWM

251  SYLSETSVSC  RSVQVLLHYF  VGTNHLWLLV  EGLYLHTLLE  PTVFPERRLW

301  PKYLVVGWAF  PMLFVIPWGF  ARAHLENTRC  WATNGNLKIW  WIIRGPMLLC

351  VTVNFFIFLK  ILKLLISKLK  AHQMCFRDYK  YRLAKSTLLL  IPLLGVHEVL

401  FTFFPDDQVQ  GFSKRIRLFI  QLTLSSVHGF  LVALQYGFAN  GEVKAELRKS

451  WGRFLLARHW  GCRTCVLGKN  FRFLGKCSKK  LSEGDGSETL  QKLRFSTCSS

501  HLASETLGDV  GVQPHRGRGA  WPRGSSLSES  SEGDFTLANT  MEEILEESEI
```

FIGURE 2

HGLP2 Human GLP-2 Receptor C4-4 vs C9-2R PCR from Clone HHT13

```
  1 TCCTTCTCTC TTATCTCCCT CTTCCTGGCT CTCACCCTCC TCTTGTTTCT
 51 TCGAAAACTC CACTGCACGC GCAACTACAT CCACATCAAC TTGTTTGCTT
101 CTTTCATCCT GAGAACCCTG GCTGTACTGC TGAAGGACGT CGTCTTCTAC
151 AACTCTTACT CCAAGAGGCC TGACAATGAG AATGGGTGGA TGTCCTACCT
201 GTCAGAGATG TCCACCTCCT GCCGCTCAGT CCAGGTTCTC TTGCATTACT
251 TTGTGGGTGC CAATTACTTA TGGCTGCTGG TTGAAGGCCT CTACCTCCAC
301 ACGCTGCTGG AGCCCACAGT GCTTCCTGAG AGGCGGCTGT GGCCCAAATA
351 CCTGCTGTTG GGTTGGGCCT TCCCTGTGCT ATTTGTTGTA CCCTGGGGTT
401 TCGCCCGTGC ACACCTGGAA AACACAGGGT GCTGGACAAC AAATGGGAAT
451 AAGAAAATCT GGTGGATCAT CCGAGGACCC ATGATGCTCT GTGTAACAGT
501 CAATTTCTTC ATCTTCCTGA AAATTCTCAA GCTTCTCATT TCTAAGCTCA
551 AAGCTCATCA AATGTGCTTC AGAGATTATA AATACAGATT GGCAAATCA
601 ACACTGGTCC TCATTCCTTT ATTGGGCGTT CATGAGATCC TCTTCTCTTT
651 CATCACTGAT GATCAAG
```

Figure 4

```
        S  F  S  L  I  S  L  F  L  A  L  T  L  L  L  P  L  K  L
        TCCTTCTCTCTTATCTCCCTCTTCCTGGCTCTCACCCTCCTCTTGTTCTTCGAAAACTC
   1    ----------+---------+---------+---------+---------+---------+   60

H  C  T  R  N  Y  I  H  M  N  L  F  A  S  F  I  L  R  T  L
        CACTGCACGCGCAACTACATCCACATGAACTTGTTTGCTTCTTTCATCCTGAGAACCCTG
  61    ----------+---------+---------+---------+---------+---------+  120

A  V  L  V  K  D  V  V  F  Y  N  S  Y  S  K  R  P  D  N  E
        GCTGTACTGGTGAAGGACGTCGTCTTCTACAACTCTTACTCCAAGAGGCCTGACAATGAG
 121    ----------+---------+---------+---------+---------+---------+  180

N  G  W  M  S  Y  L  S  E  M  S  T  S  C  R  S  V  Q  V  L
        AATGGGTGGATGTCCTACCTGTCAGAGATGTCAACCTCCTGCCGCTCAGTCCAGGTTCTC
 181    ----------+---------+---------+---------+---------+---------+  240

L  H  Y  F  V  G  A  N  Y  L  W  L  L  V  E  G  L  Y  L  H
        TTGCATTACTTTGTGGGTGCCAATTACTTATGGCTGCTGGTTGAAGGCCTCTACCTCCAC
 241    ----------+---------+---------+---------+---------+---------+  300

T  L  L  E  P  T  V  L  P  E  R  R  L  W  P  K  Y  L  L  L
        ACGCTGCTGGAGCCCACAGTGCTTCCTGAGAGGCGGCTGTGGCCCAAATACCTGCTGTTG
 301    ----------+---------+---------+---------+---------+---------+  360

G  W  A  F  P  V  L  F  V  V  P  W  G  F  A  P  A  H  L  E
        GGTTGGGCCTTCCCTGTGCTATTTGTTGTACCCTGGGGTTTCGCCCCTGCACACCTGGAA
 361    ----------+---------+---------+---------+---------+---------+  420

N  T  G  C  W  T  T  N  G  N  K  K  I  N  W  I  I  R  G  P
        AACACAGGTGCTGGACAACAAATGGGAATAAGAAAATCTGGTGGATCATCCGAGGACCC
 421    ----------+---------+---------+---------+---------+---------+  480

M  M  L  C  V  T  V  N  F  F  I  F  L  K  I  L  K  L  L  I
        ATGATGCTCTGTGTGTAACAGTCAATTTCTTCATCTTCCTGAAAATTCTCAAGCTTCTCATT
 481    ----------+---------+---------+---------+---------+---------+  540

S  K  L  K  A  H  Q  M  C  F  R  D  Y  K  Y  R  L  A  K  S
        TCTAAGCTCAAAGCTCATCAAATGTGCTTCAGAGATTATAAATACAGATTGGCAAAATCA
 541    ----------+---------+---------+---------+---------+---------+  600

T  L  V  L  I  P  L  L  G  V  H  E  I  L  F  S  F  I  T  D
        ACACTGGTCCTCATTCCTTTATTGGGCGTTCATGAGATCCTCTTCTCTTTCATCACTGAT
 601    ----------+---------+---------+---------+---------+---------+  660

D  Q
        GATCAAG
 661    -------   667
```

Figure 5

(SEQ ID NO: 11)

```
     TGGAGAGGATTTGTGCAAACATTTCTTCTGTGGACCAAGAGGAATGCAAGAGGAGGCTGC
1    ------------+---------+---------+---------+---------+---------+    60

CTGCGGTGCATCTTGGACGGCTAGAGAGATGTACCCCTACTTGTGAAGGTGCACGAGGAA
61   ------------+---------+---------+---------+---------+---------+    120

M  K  L  G  S  S  R  A  G  P  G  R  G  S  A  G  L  L  P  G
     GATCAAGCTGGGATCGAGCAGGGCAGGGCCTGGGAGAGGAAGCGCGGGACTCCTGCCTGG
121  ------------+---------+---------+---------+---------+---------+    180

V  H  E  L  P  M  G  I  P  A  P  W  G  T  S  P  L  S  F  H
     CGTCCACGAGCTGCCCATGGGCATCCCTGCCCCCTGGGGGACCAGTCCTCTCTCCTTCCA
181  ------------+---------+---------+---------+---------+---------+    240

R  K  C  S  L  W  A  P  G  R  P  F  L  T  L  V  L  L  V  S
     CAGGAAGTGCTCTCTCTGGGCCCCTGGAGGCCCTTCCTCACTCTGGTCCTGCTGGTTTC
241  ------------+---------+---------+---------+---------+---------+    300

I  K  Q  V  T  G  S  L  L  E  E  T  T  R  K  W  A  Q  Y  K
     CATCAAGCAAGTTACAGGATCCCTCCTTGAGGAAACGACTCGGAAGTGGGCTCAGTACAA
301  ------------+---------+---------+---------+---------+---------+    360

Q  A  C  L  R  D  L  L  K  E  P  S  G  I  F  C  N  G  T  F
     ACAGGCATGTCTGAGAGACTTACTCAAGGAACCTTCTGGCATATTTTGTAACGGGACATT
361  ------------+---------+---------+---------+---------+---------+    420

D  Q  Y  V  C  W  P  H  S  S  P  G  N  V  S  V  P  C  P  S
     TGATCAGTACGTGTGTTGGCCTCATTCTTCTCCTGGAAATGTCTCTGTACCCTGCCCTTC
421  ------------+---------+---------+---------+---------+---------+    480

Y  L  P  W  W  S  E  E  S  S  G  R  A  Y  R  H  C  L  A  Q
     ATACTTACCTTGGTGGAGTGAAGAGAGCTCAGGAAGGGCCTACAGACACTGCTTGGCTCA
481  ------------+---------+---------+---------+---------+---------+    540

G  T  W  Q  T  I  E  N  A  T  D  I  W  Q  D  D  S  E  C  S
     GGGGACTTGGCAGACGATAGAGAACGCCACGGATATTTGGCAGGATGACTCCGAATGCTC
541  ------------+---------+---------+---------+---------+---------+    600

E  N  H  S  F  K  Q  N  V  D  R  Y  A  L  L  S  T  L  Q  L
     CGAGAACCACAGCTTCAAGCAAAACGTGGACCGTTATGCCTTGCTGTCAACCTTGCAGCT
601  ------------+---------+---------+---------+---------+---------+    660

M  Y  T  V  G  Y  S  F  S  L  I  S  L  F  L  A  L  T  L  L
     GATGTACACCGTGGGATACTCCTTCTCTCTTATCTCCCTCTTCCTGGCTCTCACCCTCCT
661  ------------+---------+---------+---------+---------+---------+    720

L  F  L  R  K  L  H  C  T  R  N  Y  I  H  M  N  L  F  A  S
     CTTGTTTCTTCGAAAACTCCACTGCACGCGCAACTACATCCACATGAACTTGTTTGCTTC
721  ------------+---------+---------+---------+---------+---------+    780

F  I  L  R  T  L  A  V  L  V  K  D  V  V  F  Y  N  S  Y  S
     TTTCATCCTGAGAACCCTGGCTGTACTGGTGAAGGACGTCGTCTTCTACAACTCTTACTC
781  ------------+---------+---------+---------+---------+---------+    840

K  R  P  D  N  E  N  G  W  M  S  Y  L  S  E  M  S  T  S  C
     CAAGAGGCCTGACAATGAGAATGGGTGGATGTCCTACCTGTCAGAGATGTCCACCTCCTG
841  ------------+---------+---------+---------+---------+---------+    900

R  S  V  Q  V  L  L  H  Y  F  V  G  A  N  Y  L  W  L  L  V
     CCGCTCAGTCCAGGTTCTCTTGCATTACTTTGTGGGTGCCAATTACTTATGGCTGCTGGT
901  ------------+---------+---------+---------+---------+---------+    960

E  G  L  Y  L  H  T  L  L  E  P  T  V  L  P  E  R  R  L  W
     TGAAGGCCTCTACCTCCACACGCTGCTGGAGCCCACAGTGCTTCCTGAGAGGCGGCTGTG
961  ------------+---------+---------+---------+---------+---------+    1020
```

FIGURE 6A

```
              P  R  Y  L  L  L  G  W  A  F  P  V  L  F  V  V  P  W  G  F
              GCCCAGATACCTGCTGTTGGGTTGGGCCTTCCCTGTGCTATTTGTTGTACCCTGGGGTTT
      1021    ------------+---------+---------+---------+---------+---------+    1080

A  R  A  H  L  E  N  T  G  C  W  T  T  N  G  N  K  K  I  W
              CGCCCGTGCACACCTGGAGAACACAGGGTGCTGGACAACAAATGGGAATAAGAAAATCTG
      1081    ------------+---------+---------+---------+---------+---------+    1140

W  I  I  R  G  P  M  M  L  C  V  T  V  N  F  F  I  F  L  K
              GTGGATCATCCGAGGACCCATGATGCTCTGTGTAACAGTCAATTTCTTCATCTTCCTGAA
      1141    ------------+---------+---------+---------+---------+---------+    1200

I  L  K  L  L  I  S  K  L  K  A  H  Q  M  C  F  R  D  Y  K
              AATTCTCAAGCTTCTCATTTCTAAGCTCAAAGCTCATCAAATGTGCTTCAGAGATTATAA
      1201    ------------+---------+---------+---------+---------+---------+    1260

Y  R  L  A  K  S  T  L  V  L  I  P  L  L  G  V  H  E  I  L
              ATACAGATTGGCAAAATCAACACTGGTCCTCATTCCTTTATTGGGCGTTCATGAGATCCT
      1261    ------------+---------+---------+---------+---------+---------+    1320

F  S  F  I  T  D  D  Q  V  E  G  F  A  K  L  I  R  L  F  I
              CTTCTCTTTCATCACTGATGATCAAGTTGAAGGATTTGCAAAACTTATACGACTTTTCAT
      1321    ------------+---------+---------+---------+---------+---------+    1380

Q  L  T  L  S  S  F  H  G  F  L  V  A  L  Q  Y  G  F  A  N
              TCAGTTGACACTGAGCTCCTTTCATGGGTTCCTGGTGGCCTTGCAGTATGGTTTTGCCAA
      1381    ------------+---------+---------+---------+---------+---------+    1440

G  E  V  K  A  E  L  R  K  Y  W  V  R  F  L  L  A  R  H  S
              TGGAGAAGTGAAGGCTGAGCTGCGGAAATACTGGGTCCGCTTCTTGCTAGCCCGCCACTC
      1441    ------------+---------+---------+---------+---------+---------+    1500

G  C  R  A  C  V  L  G  K  D  F  R  F  L  G  K  C  P  K  K
              AGGCTGCAGAGCCTGTGTCCTGGGGAAGGACTTCCGGTTCCTAGGAAAATGTCCCAAGAA
      1501    ------------+---------+---------+---------+---------+---------+    1560

L  S  E  G  D  G  A  E  K  L  R  K  L  Q  P  S  L  N  S  G
              GCTCTCGGAAGGAGATGGCGCTGAGAAGCTTCGGAAGCTGCAGCCCTCACTTAACAGTGG
      1561    ------------+---------+---------+---------+---------+---------+    1620

R  L  L  H  L  A  M  R  G  L  G  E  L  G  A  Q  P  Q  Q  D
              GCGGCTCCTACATCTAGCCATGCGAGGTCTTGGGGAGCTGGGCGCCCAGCCCCAACAGGA
      1621    ------------+---------+---------+---------+---------+---------+    1680

H  A  R  W  P  R  G  S  S  L  S  E  C  S  E  G  D  V  T  M
              CCATGCACGCTGGCCCCGGGGCAGCAGCCTGTCCGAGTGCAGTGAGGGGATGTCACCAT
      1681    ------------+---------+---------+---------+---------+---------+    1740

A  N  T  M  E  E  I  L  E  E  S  E  I  *
              GGCCAACACCATGGAGGAGATTCTGGAAGAGAGTGAGATCTAGGGTGGAGTTCCACCACC
      1741    ------------+---------+---------+---------+---------+---------+    1800

CTGGCTCTGCTCCCAGGGACTCTTGAGGGGGCCCAGGAAGAGGAAGCAAAGCAGGACACA
      1801    ------------+---------+---------+---------+---------+---------+    1860

CGTTGCTGGGCACGGAATCATTCTCGTTCCATTCACCATGCCACTTTGATATGAAAGCTA
      1861    ------------+---------+---------+---------+---------+---------+    1920

TCACAAGGTTCTTCAAGCTCTGTATGAAAGAGGCTGTGTGTCATGCTCACAGCCTCTGCC
      1921    ------------+---------+---------+---------+---------+---------+    1980

TGCTCTTCTCATCCTAATAACCCCCACCAGTGTGTTTTCCACAATGCCCACCAGACCCTA
      1981    ------------+---------+---------+---------+---------+---------+    2040

GGGCCTGGCTCTAAATTCAAGCCAATGAAGTCCCACCCGGAATTCTTTTGCTTTTTACCC
      2041    ------------+---------+---------+---------+---------+---------+    2100

CTGGAAGAAATA
      2101    ----------+--    2112
```

FIGURE 6B

Human GLP-2 Receptor Complete Open Reading Frame
Note: Translation may start with M-1 or M-25.
Length: 553  April 21, 1997 07:42  Type: P  Check: 2776

```
  1  MKLGSSRAGP GRGSAGLLPG VHELPMGIPA PWGTSPLSFH RKCSLWAPGR
 51  PFLTLVLLVS IKQVTGSLLE ETTRKWAQYK QACLRDLLKE PSGIFCNGTF
101  DQYVCWPHSS PGNVSVPCPS YLPWWSEESS GRAYRHCLAQ GTWQTIENAT
151  DIWQDDSECS ENHSFKQNVD RYALLSTLQL MYTVGYSFSL ISLFLALTLL
201  LFLRKLHCTR NYIHMNLFAS FILRTLAVLV KDVVFYNSYS KRPDNENGWM
251  SYLSEMSTSC RSVQVLLHYF VGANYLWLLV EGLYLHTLLE PTVLPERRLW
301  PRYLLLGWAF PVLFVVPWGF ARAHLENTGC WTTNGNKKIW WIIRGPMMLC
351  VTVNFFIFLK ILKLLISKLK AHQMCFRDYK YRLAKSTLVL IPLLGVHEIL
401  FSFITDDQVE GFAKLIRLFI QLTLSSFHGF LVALQYGFAN GEVKAELRKY
451  WVRFLLARHS GCRACVLGKD FRFLGKCPKK LSEGDGAEKL RKLQPSLNSG
501  RLLHLAMRGL GELGAQPQQD HARWPRGSSL SECSEGDVTM ANTMEEILEE
551  SEI
```

FIGURE 7

```
  1 MRPQPSPAVPSRCREAPVPRVRAQPVGIPEAQGPVPLHSQQMRLLWGPGR  50
    |:   | | |    .| |   |.|||  | ||   .    || |||
  1 MKLGSSRAGPGRGSAGLLPGVHELPMGIPAPWGTSPLSFHRKCSLWAPGR  50

51 PFLALLLLVSIKQVTGSLLKETTQKWANYKEKCLEDLHNRLSGIFCNGTF 100
    ||| |.|||||||||||||-|||.|||  ||:  || ||    |||||||||
 51 PFLTLVLLVSIKQVTGSLLEETTRKWAQYKQACLRDLLKEPSGIFCNGTF 100

101 DRYVCWPHSYPGNVSVPCPSYLPWWNAESPGRAYRHCLAQGTWQTRENTT 150
    |.|||||| |||||||||||||||||.  ||  ||||||||||||||| || |
101 DQYVCWPHSSPGNVSVPCPSYLPWWSEESSGRAYRHCLAQGTWQTIENAT 150

151 DIWQDESECSENHSFRQNVDHYALLYTLQLMYTVGYSVSLISLFLALTLF 200
    ||||:|||||||||:||||  ||||  ||||||||||||  ||||||||||  ||||||||||
151 DIWQDDSECSENHSFKQNVDRYALLSTLQLMYTVGYSFSLISLFLALTLL 200

201 LFLRKLHCTRNYIHMNLFASFILKVLAVLVKDMVSHNSYSKRPDDESGWM 250
    ||||||||||||||||||||||||:  |||||||.|  :|||||||||.|.|||
201 LFLRKLHCTRNYIHMNLFASFILRTLAVLVKDVVFYNSYSKRPDNENGWM 250

251 SYLSETSVSCRSVQVLLHYFVGTNHLWLLVEGLYLHTLLEPTVFPERRLW 300
    |||||  |  |||||||||||||||| |:|||||||||||||||||||| ||||||
251 SYLSEMSTSCRSVQVLLHYFVGANYLWLLVEGLYLHTLLEPTVLPERRLW 300

301 PKYLVVGWAFPMLFVIPWGFARAHLENTRCWATNGNLKIWWIIRGPMLLC 350
    |:||..|||||.|||:|||||||||||||| || ||||  ||||||||||:||
301 PRYLLLGWAFPVLFVVPWGFARAHLENTGCWTTNGNKKIWWIIRGPMMLC 350

351 VTVNFFIFLKILKLLISKLKAHQMCFRDYKYRLAKSTLLLIPLLGVHEVL 400
    |||||||||||||||||||||||||||||||||||||||||||.|||||||||:|
351 VTVNFFIFLKILKLLISKLKAHQMCFRDYKYRLAKSTLVLIPLLGVHEIL 400

401 FTFFPDDQVQGFSKRIRLFIQLTLSSVHGFLVALQYGFANGEVKAELRKS 450
    |.|  ||||:||.|  ||||||||||  |||||||||||||||||||||||||||
401 FSFITDDQVEGFAKLIRLFIQLTLSSFHGFLVALQYGFANGEVKAELRKY 450

451 WGRFLLARHWGCRTCVLGKNFRFLGKCSKKLSEGDGSETLQKLRFSTCSS 500
    |  |||||||  ||| |||||.|||||||||||  |.||.  | |
451 WVRFLLARHSGCRACVLGKDFRFLGKCPKKLSEGDGAEKLRKLQPSLNSG 500

501 ...HLASETLGDVGVQPHRGRGAWPRGSSLSESSEGDFTLANTMEEILEE 547
       |||    ||:.| ||  .    |||||||||  ||||  |:||||||||||
501 RLLHLAMRGLGELGAQPQQDHARWPRGSSLSECSEGDVTMANTMEEILEE 550

548 SEI 550
    |||
551 SEI 553
```

FIGURE 9

```
GL2R_RAT_R    MRPQPSPAVPSRCREAPVPRVRAQPVGIPEAQGPVPLHSQQMRLLWGPG-RPFLALLLLV
HWBRPAT_TR    MKLGSSRAGPGRGSAGLLPGVHELPMGIPAPWGTSPLSFHRKCSLWAPG-RPFLTLVLLV
GLPR_HUMAN    ------------------------------MAGAPGPLRLALLLLGMVGRAGPRP--------
                                            .  *  *     .   * **

GL2R_RAT_R    SIKQVTGSLLKETTQKWANYKEKCLEDLHNRL---SGIFCNGTFDRYVCWPHSYPG-NVS
HWBRPAT_TR    SIKQVTGSLLEETTRKWAQYKQACLRDLLKEP---SGIFCNGTFDQYVCWPHSSPG-NVS
GLPR_HUMAN    ---QGATVSLWETVQKWREYRRQCQRSLTEDPPPATDLFCNRTFDEYACWPDGEPGSFVN
                 * .   *  ** .**  *.  *     *     .***  *** *  ***   **   *

GL2R_RAT_R    VPCPSYLPWWNAESPGRAYRHCLAQGTWQTRENTTDIWQDESECSENHSFRQNVDHYALL
HWBRPAT_TR    VPCPSYLPWWSEESSGRAYRHCLAQGTWQTIENATDIWQDDSECSENHSFKQNVDRYALL
GLPR_HUMAN    VSCPWYLPWASSVPQGHVYRFCTAEGLWLQKDNSSLPWRDLSECEESKRGERSSPEEQLL
              * ** ****        *. ** * *.*    .*..   *.*  *** *  .     **

GL2R_RAT_R    YTLQLMYTVGYSVSLISLFLALTLFLFLRKLHCTRNYIHMNLFASFILKVLAVLVKDMVS
HWBRPAT_TR    STLQLMYTVGYSFSLISLFLALTLLLLFLRKLHCTRNYIHMNLFASFILRTLAVLVKDVVF
GLPR_HUMAN    F-LYIIYTVGYALSFSALVIASAILLGFRHLHCTRNYIHLNLFASFILRALSVFIKDAAL
                 ..*****. *   .*  .*  .*  ..  *  *.********.*******.  *.*   **

GL2R_RAT_R    HNSYSKRPDDESGWMSYLS-ETSVSCRSVQVLLHYFVGTNHLWLLVEGLYLHTLLEPTVF
HWBRPAT_TR    YNSYSKRPDNENGWMSYLS-EMSTSCRSVQVLLHYFVGANYLWLLVEGLYLHTLLEPTVL
GLPR_HUMAN    KWMYST-AAQQHQWDGLLSYQDSLSCRLVFLLMQYCVAANYYWLLVEGVYLYTLLAFSVF
                **     .   *    **  . *** * .*..* *  .*     ******.**  ***   .*

GL2R_RAT_R    PERRLWPKYLVVGWAFPMLFVIPWGFARAHLENTRCWATNGNLKIWWIIRGPMLLCVTVN
HWBRPAT_TR    PERRLWPRYLLLGWAFPVLFVVPWGFARAHLENTGCWTTNGNKKIWWIIRGPMMLCVTVN
GLPR_HUMAN    SEQWIFRLYVSIGWGVPLLFVVPWGIVKYLYEDEGCWTRNSNMNYWLIIRLPILFAIGVN
              *..    *. .**  ****.***    *   **.*   *  *  ***  *      **

GL2R_RAT_R    FFIFLKILKLLISKLKAHQMCFRDYKYRLAKSTLLLIPLLGVHEVLFTFFPDDQVQGFSK
HWBRPAT_TR    FFIFLKILKLLISKLKAHQMCFRDYKYRLAKSTLVLIPLLGVHEILFSFITDDQVEGFAK
GLPR_HUMAN    FLIFVRVICIVVSKLKANLMCKTDIKCRLAKSTLTLIPLLGTHEVIFAFVMDEHARGTLR
              * **....  ...*****.  **  * * *******  ***** **..*.*   *  .

GL2R_RAT_R    RIRLFIQLTLSSVHGFLVALQYGFANGEVKAELRKSWGRFLLARHWGCRTCVLGKNFRFL
HWBRPAT_TR    LIRLFIQLTLSSFHGFLVALQYGFANGEVKAELRKYWVRFLLARHSGCRACVLGKDFRFL
GLPR_HUMAN    FIKLFTELSFTSFQGLMVAILYCFVNNEVQLEFRKSWERWRLEHLHIQRDSSMKP-----
              *.** .... ...*** *   *.**. * **. * ***  *  ** *  .*.*   *  ..   .

GL2R_RAT_R    GKCSKKLSEGDGSETLQKLRFSTCSS---HLASETLGDVGVQPHRGRGAWPRGSSLSESS
HWBRPAT_TR    GKCPKKLSEGDGAEKLRKLQPSLNSGRLLHLAMRGLGELGAQPQQDHARWPRGSSLSECS
GLPR_HUMAN    LKCPTSS-LSSGATAGSSMYTATCQASCS-------------------------------
               **          *.    . .    .

GL2R_RAT_R    EGDFTLANTMEEILEESEI
HWBRPAT_TR    EGDVTMANTMEEILEESEI
GLPR_HUMAN    -------------------
```

FIGURE 10

SEQUENCE LISTING

<160> NUMBER OF SEQ ID NOS: 28

<210> SEQ ID NO 1
<211> LENGTH: 2575
<212> TYPE: DNA
<213> ORGANISM: Rattus norvegicus

<400> SEQUENCE: 1

```
aagcttcgcg gcctctgcag akgacttgtg caaacacttc ctctctggac aaggaggaat      60
gcaggaggcc accgcctgca gtacatcttg gagtgttgga gggatgtgcc tgcacttgtg     120
aacgggcgcc aggagaatga ggccccaacc aagcccggca gtgcccagta gatgcagaga     180
```

```
ggcacccgtg ccccgagtga gggcacagcc agtgggcatc cctgaggccc aggggcccgt      240
tcctctccac tcccaacaga tgcgtctgct gtggggccct gggaggccct tcctcgccct      300
gcttctgctg gtttccatca agcaagttac aggatcgctc ctcaaggaga caactcagaa      360
gtgggctaat tataaggaga agtgtctgga agacttgcac aatagacttt ctggcatatt      420
ttgtaatggg acatttgatc ggtatgtgtg ctggcctcat tcttatcctg gaaatgtctc      480
tgttccctgt ccttcatact taccttggtg gaatgcagag agcccaggaa gggcctacag      540
acactgcttg gctcagggga cttggcagac gcgagagaac accacagata tttggcagga      600
tgaatcagaa tgctcagaga accacagctt cagacaaaac gtggatcact acgccttgct      660
atacaccttg cagctgatgt acactgtggg ctactccgtg tctctcatct ccctcttctt      720
ggctcttaca ctcttcttgt tccttcgaaa actgcattgc acacgcaatt acatccacat      780
gaacctgttc gcttcgttca tcctgaaagt tctggctgtc ctggtgaagg acatggtctc      840
ccacaactct tactccaaga ggcccgatga tgagagtgga tggatgtcat atctgtcaga      900
gacatccgtc tcctgtcgct ccgtccaggt cctcctgcac tactttgtgg gcaccaatca      960
cttgtggctg ctggttgaag actttacct ccacactctg ctggagccca cagtgtttcc      1020
tgaaaggcgg ctgtggccca gtacctggt ggtgggttgg gccttcccca tgctgttgt      1080 tattccctgg ggttttgccc gtgcacacct ggagaacaca cggtgctggg ccacaaatgg      1140
gaacctgaaa atctggtgga tcatcagagg acccatgctg ctttgtgtaa cagttaattt      1200
cttcatcttc ctcaagattc tcaagcttct catttctaag ctcaaagctc atcagatgtg      1260
cttcagagac tacaaataca gattggcgaa atcaacgttg ctcctcattc ctttgttggg      1320
ggttcatgag gtcctcttca ctttcttccc cgacgaccaa gttcaaggat tttcaaaacg      1380
tattcgactc ttcatccagc tgacactgag ctctgtccac ggattttctgg tggccttgca      1440 gtatggctt gccaatggag aggtgaaggc agagctgcga aagtcatggg ccgcttctt      1500 attagcccgc cactggggct gcagaacctg tgtcctgggg aagaatttcc ggttcctggg      1560
gaagtgttcc aagaagctgt cggagggaga tggctctgag acactccaga agctgcggtt      1620
ctccacatgc agctcacacc tggcctctga cccctggga gacgttgggg tacagcctca      1680
caggggccgt ggagcttggc cccggggaag cagcctgtct gagagcagtg agggagactt      1740
caccctggcc aatacgatgg aggagattct ggaagagagt gagatctaag gcagggtcca      1800
tcaccgcagc ttggccactg argamccaac cctargaagg atkttgccga rcccarggtc      1860
ctcctcttcc tatgtwctat mcccattttg atgtgaagtc tctcctgggt gamcaasctc      1920
tgtaccaacs artctcagtc cctcttgccc ttgtcaccct actaccctc ccccatcaca      1980 catgttttcc agaatktccg ttggtttggg ggggggggtc ttgccctaaa ttcaagtsga      2040
gtggarccca ccatgaagaa aartcattta ttaaatagar tccggttagg atctccttcc      2100
cgttcatggt gcatggcctc cttccaaggg atgggagtcg gstgcactgg aaccccacag      2160
gaaactttga agtatccagt tctagggaat tatagccaat attctgagag agcaagtctg      2220
agatgagakc cgagaatwgc aagtgtwgga cawgcattca aggaaactcc tcacctttgg      2280
gcgaaaccta tggcaggatc ggcatggagc agctattmtg caayggccgc tcacctggga      2340
cataccactc tccttgggca ggatgtgacc ccatgtkgtc ccccagactc ctctcctcct      2400
tgcttststt cytttccygt caagtctcac ctcccttct acatctcagt tcwgtttggt      2460
gtygacagaa gyytgaatgt cacaatactg catgtgttag tttctgtcgt cattgctgtg      2520
```
tccaaatacc tgaccaggac caatttaagc gaggaactgc tacatgggcg gccgc        2575

<210> SEQ ID NO 2
<211> LENGTH: 550
<212> TYPE: PRT
<213> ORGANISM: Rattus norvegicus

<400> SEQUENCE: 2

```
Met Arg Pro Gln Pro Ser Pro Ala Val Pro Ser Arg Cys Arg Glu Ala
 1               5                  10                  15

Pro Val Pro Arg Val Arg Ala Gln Pro Val Gly Ile Pro Glu Ala Gln
                20                  25                  30

Gly Pro Val Pro Leu His Ser Gln Gln Met Arg Leu Leu Trp Gly Pro
            35                  40                  45

Gly Arg Pro Phe Leu Ala Leu Leu Leu Val Ser Ile Lys Gln Val
        50                  55                  60

Thr Gly Ser Leu Leu Lys Glu Thr Thr Gln Lys Trp Ala Asn Tyr Lys
65                  70                  75                  80

Glu Lys Cys Leu Glu Asp Leu His Asn Arg Leu Ser Gly Ile Phe Cys
                85                  90                  95

Asn Gly Thr Phe Asp Arg Tyr Val Cys Trp Pro His Ser Tyr Pro Gly
            100                 105                 110

Asn Val Ser Val Pro Cys Pro Ser Tyr Leu Pro Trp Trp Asn Ala Glu
        115                 120                 125

Ser Pro Gly Arg Ala Tyr Arg His Cys Leu Ala Gln Gly Thr Trp Gln
    130                 135                 140

Thr Arg Glu Asn Thr Thr Asp Ile Trp Gln Asp Glu Ser Glu Cys Ser
145                 150                 155                 160

Glu Asn His Ser Phe Arg Gln Asn Val Asp His Tyr Ala Leu Leu Tyr
                165                 170                 175

Thr Leu Gln Leu Met Tyr Thr Val Gly Tyr Ser Val Ser Leu Ile Ser
            180                 185                 190

Leu Phe Leu Ala Leu Thr Leu Phe Leu Phe Leu Arg Lys Leu His Cys
        195                 200                 205

Thr Arg Asn Tyr Ile His Met Asn Leu Phe Ala Ser Phe Ile Leu Lys
    210                 215                 220

Val Leu Ala Val Leu Val Lys Asp Met Val Ser His Asn Ser Tyr Ser
225                 230                 235                 240

Lys Arg Pro Asp Asp Glu Ser Gly Trp Met Ser Tyr Leu Ser Glu Thr
                245                 250                 255

Ser Val Ser Cys Arg Ser Val Gln Val Leu Leu His Tyr Phe Val Gly
            260                 265                 270

Thr Asn His Leu Trp Leu Leu Val Glu Gly Leu Tyr Leu His Thr Leu
        275                 280                 285

Leu Glu Pro Thr Val Phe Pro Glu Arg Arg Leu Trp Pro Lys Tyr Leu
    290                 295                 300

Val Val Gly Trp Ala Phe Pro Met Leu Phe Val Ile Pro Trp Gly Phe
305                 310                 315                 320

Ala Arg Ala His Leu Glu Asn Thr Arg Cys Trp Ala Thr Asn Gly Asn
                325                 330                 335

Leu Lys Ile Trp Trp Ile Ile Arg Gly Pro Met Leu Leu Cys Val Thr
            340                 345                 350

Val Asn Phe Phe Ile Phe Leu Lys Ile Leu Lys Leu Leu Ile Ser Lys
        355                 360                 365
```

Leu Lys Ala His Gln Met Cys Phe Arg Asp Tyr Lys Tyr Arg Leu Ala
    370                 375                 380

Lys Ser Thr Leu Leu Leu Ile Pro Leu Leu Gly Val His Glu Val Leu
385                 390                 395                 400

Phe Thr Phe Phe Pro Asp Asp Gln Val Gln Gly Phe Ser Lys Arg Ile
                405                 410                 415

Arg Leu Phe Ile Gln Leu Thr Leu Ser Ser Val His Gly Phe Leu Val
                420                 425                 430

Ala Leu Gln Tyr Gly Phe Ala Asn Gly Glu Val Lys Ala Glu Leu Arg
            435                 440                 445

Lys Ser Trp Gly Arg Phe Leu Leu Ala Arg His Trp Gly Cys Arg Thr
    450                 455                 460

Cys Val Leu Gly Lys Asn Phe Arg Phe Leu Gly Lys Cys Ser Lys Lys
465                 470                 475                 480

Leu Ser Glu Gly Asp Gly Ser Glu Thr Leu Gln Lys Leu Arg Phe Ser
                485                 490                 495

Thr Cys Ser Ser His Leu Ala Ser Glu Thr Leu Gly Asp Val Gly Val
                500                 505                 510

Gln Pro His Arg Gly Arg Gly Ala Trp Pro Arg Gly Ser Ser Leu Ser
            515                 520                 525

Glu Ser Ser Glu Gly Asp Phe Thr Leu Ala Asn Thr Met Glu Glu Ile
    530                 535                 540

Leu Glu Glu Ser Glu Ile
545                 550

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)
<223> OTHER INFORMATION: a, c, g, t, unknown, or other

<400> SEQUENCE: 3
tttttctaga asrtsatsta cacngtsggc tac                                33

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttttctcgag ccarcarcca sswrtarttg gc                                 32

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aactacatcc acmkgmayct gttyvygtcb ttcatsct                           38

-continued

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcatctccct cttcttggct cttac                                              25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tctgacagat atgacatcca tccac                                              25

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (5)
<223> OTHER INFORMATION: a, c, g, t, unknown, or other

<400> SEQUENCE: 8
tcyrnctgsa cctcmyyrtt gasraarcag ta                                      32

<210> SEQ ID NO 9
<211> LENGTH: 667
<212> TYPE: DNA
<213> ORGANISM: Homo sapiens
<220> FEATURE:
<221> NAME/KEY: CDS
<222> LOCATION: (1)..(666)

<400> SEQUENCE: 9 tcc ttc tct ctt atc tcc ctc ttc ctg gct ctc acc ctc ctc ttg ttt         48
Ser Phe Ser Leu Ile Ser Leu Phe Leu Ala Leu Thr Leu Leu Leu Phe
 1               5                  10                  15 ctt cga aaa ctc cac tgc acg cgc aac tac atc cac atg aac ttg ttt         96
Leu Arg Lys Leu His Cys Thr Arg Asn Tyr Ile His Met Asn Leu Phe
             20                  25                  30 gct tct ttc atc ctg aga acc ctg gct gta ctg gtg aag gac gtc gtc        144
Ala Ser Phe Ile Leu Arg Thr Leu Ala Val Leu Val Lys Asp Val Val
         35                  40                  45 ttc tac aac tct tac tcc aag agg cct gac aat gag aat ggg tgg atg        192
Phe Tyr Asn Ser Tyr Ser Lys Arg Pro Asp Asn Glu Asn Gly Trp Met
     50                  55                  60 tcc tac ctg tca gag atg tcc acc tcc tgc cgc tca gtc cag gtt ctc        240
Ser Tyr Leu Ser Glu Met Ser Thr Ser Cys Arg Ser Val Gln Val Leu
 65                  70                  75                  80 ttg cat tac ttt gtg ggt gcc aat tac tta tgg ctg ctg gtt gaa ggc        288
Leu His Tyr Phe Val Gly Ala Asn Tyr Leu Trp Leu Leu Val Glu Gly
                 85                  90                  95 ctc tac ctc cac acg ctg ctg gag ccc aca gtg ctt cct gag agg cgg        336

```
Leu Tyr Leu His Thr Leu Leu Glu Pro Thr Val Leu Pro Glu Arg Arg
            100                 105                 110 ctg tgg ccc ara tac ctg ctg ttg ggt tgg gcc ttc cct gtg cta ttt    384
Leu Trp Pro Xaa Tyr Leu Leu Leu Gly Trp Ala Phe Pro Val Leu Phe
        115                 120                 125 gtt gta ccc tgg ggt ttc gcc cgt gca cac ctg gar aac aca ggg tgc    432
Val Val Pro Trp Gly Phe Ala Arg Ala His Leu Glu Asn Thr Gly Cys
130                 135                 140 tgg aca aca aat ggg aat aag aaa atc tgg tgg atc atc cga gga ccc    480
Trp Thr Thr Asn Gly Asn Lys Lys Ile Trp Trp Ile Ile Arg Gly Pro
145                 150                 155                 160 atg atg ctc tgt gta aca gtc aat ttc ttc atc ttc ctg aaa att ctc    528
Met Met Leu Cys Val Thr Val Asn Phe Phe Ile Phe Leu Lys Ile Leu
                165                 170                 175 aag ctt ctc att tct aag ctc aaa gct cat caa atg tgc ttc aga gat    576
Lys Leu Leu Ile Ser Lys Leu Lys Ala His Gln Met Cys Phe Arg Asp
            180                 185                 190 tat aaa tac aga ttg gca aaa tca aca ctg gtc ctc att cct tta ttg    624
Tyr Lys Tyr Arg Leu Ala Lys Ser Thr Leu Val Leu Ile Pro Leu Leu
        195                 200                 205 ggc gtt cat gag atc ctc ttc tct ttc atc act gat gat caa g         667
Gly Val His Glu Ile Leu Phe Ser Phe Ile Thr Asp Asp Gln
    210                 215                 220

<210> SEQ ID NO 10
<211> LENGTH: 222
<212> TYPE: PRT
<213> ORGANISM: Homo sapiens
<220> FEATURE:
<221> NAME/KEY: MOD_RES
<222> LOCATION: (116)
<223> OTHER INFORMATION: Lys or Arg

<400> SEQUENCE: 10

Ser Phe Ser Leu Ile Ser Leu Phe Leu Ala Leu Thr Leu Leu Leu Phe
 1               5                  10                  15

Leu Arg Lys Leu His Cys Thr Arg Asn Tyr Ile His Met Asn Leu Phe
            20                  25                  30

Ala Ser Phe Ile Leu Arg Thr Leu Ala Val Leu Val Lys Asp Val Val
        35                  40                  45

Phe Tyr Asn Ser Tyr Ser Lys Arg Pro Asp Asn Glu Asn Gly Trp Met
    50                  55                  60

Ser Tyr Leu Ser Glu Met Ser Thr Ser Cys Arg Ser Val Gln Val Leu
65                  70                  75                  80

Leu His Tyr Phe Val Gly Ala Asn Tyr Leu Trp Leu Leu Val Glu Gly
                85                  90                  95

Leu Tyr Leu His Thr Leu Leu Glu Pro Thr Val Leu Pro Glu Arg Arg
            100                 105                 110

Leu Trp Pro Xaa Tyr Leu Leu Leu Gly Trp Ala Phe Pro Val Leu Phe
        115                 120                 125

Val Val Pro Trp Gly Phe Ala Arg Ala His Leu Glu Asn Thr Gly Cys
    130                 135                 140

Trp Thr Thr Asn Gly Asn Lys Lys Ile Trp Trp Ile Ile Arg Gly Pro
145                 150                 155                 160

Met Met Leu Cys Val Thr Val Asn Phe Phe Ile Phe Leu Lys Ile Leu
                165                 170                 175

Lys Leu Leu Ile Ser Lys Leu Lys Ala His Gln Met Cys Phe Arg Asp
            180                 185                 190
```

```
Tyr Lys Tyr Arg Leu Ala Lys Ser Thr Leu Val Leu Ile Pro Leu Leu
        195                 200                 205

Gly Val His Glu Ile Leu Phe Ser Phe Ile Thr Asp Asp Gln
210                 215                 220

<210> SEQ ID NO 11
<211> LENGTH: 2112
<212> TYPE: DNA
<213> ORGANISM: Homo sapiens
<220> FEATURE:
<221> NAME/KEY: CDS
<222> LOCATION: (122)..(1780)

<400> SEQUENCE: 11
tggagaggat tgtgcaaac atttcttctg tggaccaaga ggaatgcaag aggaggctgc      60
ctgcggtgca tcttggacgg ctagagagat gtaccctac ttgtgaaggt gcacgaggaa     120 g atg aag ctg gga tcg agc agg gca ggg cct ggg aga gga agc gcg gga   169
  Met Lys Leu Gly Ser Ser Arg Ala Gly Pro Gly Arg Gly Ser Ala Gly
   1               5                  10                  15 ctc ctg cct ggc gtc cac gag ctg ccc atg ggc atc cct gcc ccc tgg   217
Leu Leu Pro Gly Val His Glu Leu Pro Met Gly Ile Pro Ala Pro Trp
                20                  25                  30 ggg acc agt cct ctc tcc ttc cac agg aag tgc tct ctc tgg gcc cct   265
Gly Thr Ser Pro Leu Ser Phe His Arg Lys Cys Ser Leu Trp Ala Pro
        35                  40                  45 ggg agg ccc ttc ctc act ctg gtc ctg ctg gtt tcc atc aag caa gtt   313
Gly Arg Pro Phe Leu Thr Leu Val Leu Leu Val Ser Ile Lys Gln Val
 50                  55                  60 aca gga tcc ctc ctt gag gaa acg act cgg aag tgg gct cag tac aaa   361
Thr Gly Ser Leu Leu Glu Glu Thr Thr Arg Lys Trp Ala Gln Tyr Lys
 65                  70                  75                  80 cag gca tgt ctg aga gac tta ctc aag gaa cct tct ggc ata ttt tgt   409
Gln Ala Cys Leu Arg Asp Leu Leu Lys Glu Pro Ser Gly Ile Phe Cys
                85                  90                  95 aac ggg aca ttt gat cag tac gtg tgt tgg cct cat tct tct cct gga   457
Asn Gly Thr Phe Asp Gln Tyr Val Cys Trp Pro His Ser Ser Pro Gly
            100                 105                 110 aat gtc tct gta ccc tgc cct tca tac tta cct tgg tgg agt gaa gag   505
Asn Val Ser Val Pro Cys Pro Ser Tyr Leu Pro Trp Trp Ser Glu Glu
        115                 120                 125 agc tca gga agg gcc tac aga cac tgc ttg gct cag ggg act tgg cag   553
Ser Ser Gly Arg Ala Tyr Arg His Cys Leu Ala Gln Gly Thr Trp Gln
    130                 135                 140 acg ata gag aac gcc acg gat att tgg cag gat gac tcc gaa tgc tcc   601
Thr Ile Glu Asn Ala Thr Asp Ile Trp Gln Asp Asp Ser Glu Cys Ser
145                 150                 155                 160 gag aac cac agc ttc aag caa aac gtg gac cgt tat gcc ttg ctg tca   649
Glu Asn His Ser Phe Lys Gln Asn Val Asp Arg Tyr Ala Leu Leu Ser
                165                 170                 175 acc ttg cag ctg atg tac acc gtg gga tac tcc ttc tct ctt atc tcc   697
Thr Leu Gln Leu Met Tyr Thr Val Gly Tyr Ser Phe Ser Leu Ile Ser
            180                 185                 190 ctc ttc ctg gct ctc acc ctc ctc ttg ttt ctt cga aaa ctc cac tgc   745
Leu Phe Leu Ala Leu Thr Leu Leu Leu Phe Leu Arg Lys Leu His Cys
        195                 200                 205 acg cgc aac tac atc cac atg aac ttg ttt gct tct ttc atc ctg aga   793
Thr Arg Asn Tyr Ile His Met Asn Leu Phe Ala Ser Phe Ile Leu Arg
    210                 215                 220 acc ctg gct gta ctg gtg aag gac gtc gtc ttc tac aac tct tac tcc   841
Thr Leu Ala Val Leu Val Lys Asp Val Val Phe Tyr Asn Ser Tyr Ser
```

-continued

```
                 225                 230                 235                 240
aag agg cct gac aat gag aat ggg tgg atg tcc tac ctg tca gag atg         889
Lys Arg Pro Asp Asn Glu Asn Gly Trp Met Ser Tyr Leu Ser Glu Met
                245                 250                 255 tcc acc tcc tgc cgc tca gtc cag gtt ctc ttg cat tac ttt gtg ggt         937
Ser Thr Ser Cys Arg Ser Val Gln Val Leu Leu His Tyr Phe Val Gly
            260                 265                 270 gcc aat tac tta tgg ctg ctg gtt gaa ggc ctc tac ctc cac acg ctg         985
Ala Asn Tyr Leu Trp Leu Leu Val Glu Gly Leu Tyr Leu His Thr Leu
        275                 280                 285 ctg gag ccc aca gtg ctt cct gag agg cgg ctg tgg ccc aga tac ctg        1033
Leu Glu Pro Thr Val Leu Pro Glu Arg Arg Leu Trp Pro Arg Tyr Leu
    290                 295                 300 ctg ttg ggt tgg gcc ttc cct gtg cta ttt gtt gta ccc tgg ggt ttc        1081
Leu Leu Gly Trp Ala Phe Pro Val Leu Phe Val Val Pro Trp Gly Phe
305                 310                 315                 320 gcc cgt gca cac ctg gag aac aca ggg tgc tgg aca aca aat ggg aat        1129
Ala Arg Ala His Leu Glu Asn Thr Gly Cys Trp Thr Thr Asn Gly Asn
                325                 330                 335 aag aaa atc tgg tgg atc atc cga gga ccc atg atg ctc tgt gta aca        1177
Lys Lys Ile Trp Trp Ile Ile Arg Gly Pro Met Met Leu Cys Val Thr
            340                 345                 350 gtc aat ttc ttc atc ttc ctg aaa att ctc aag ctt ctc att tct aag        1225
Val Asn Phe Phe Ile Phe Leu Lys Ile Leu Lys Leu Leu Ile Ser Lys
        355                 360                 365 ctc aaa gct cat caa atg tgc ttc aga gat tat aaa tac aga ttg gca        1273
Leu Lys Ala His Gln Met Cys Phe Arg Asp Tyr Lys Tyr Arg Leu Ala
    370                 375                 380 aaa tca aca ctg gtc ctc att cct tta ttg ggc gtt cat gag atc ctc        1321
Lys Ser Thr Leu Val Leu Ile Pro Leu Leu Gly Val His Glu Ile Leu
385                 390                 395                 400 ttc tct ttc atc act gat gat caa gtt gaa gga ttt gca aaa ctt ata        1369
Phe Ser Phe Ile Thr Asp Asp Gln Val Glu Gly Phe Ala Lys Leu Ile
                405                 410                 415 cga ctt ttc att cag ttg aca ctg agc tcc ttt cat ggg ttc ctg gtg        1417
Arg Leu Phe Ile Gln Leu Thr Leu Ser Ser Phe His Gly Phe Leu Val
            420                 425                 430 gcc ttg cag tat ggt ttt gcc aat gga gaa gtg aag gct gag ctg cgg        1465
Ala Leu Gln Tyr Gly Phe Ala Asn Gly Glu Val Lys Ala Glu Leu Arg
        435                 440                 445 aaa tac tgg gtc cgc ttc ttg cta gcc cgc cac tca ggc tgc aga gcc        1513
Lys Tyr Trp Val Arg Phe Leu Leu Ala Arg His Ser Gly Cys Arg Ala
    450                 455                 460 tgt gtc ctg ggg aag gac ttc cgg ttc cta gga aaa tgt ccc aag aag        1561
Cys Val Leu Gly Lys Asp Phe Arg Phe Leu Gly Lys Cys Pro Lys Lys
465                 470                 475                 480 ctc tcg gaa gga gat ggc gct gag aag ctt cgg aag ctg cag ccc tca        1609
Leu Ser Glu Gly Asp Gly Ala Glu Lys Leu Arg Lys Leu Gln Pro Ser
                485                 490                 495 ctt aac agt ggg cgg ctc cta cat cta gcc atg cga ggt ctt ggg gag        1657
Leu Asn Ser Gly Arg Leu Leu His Leu Ala Met Arg Gly Leu Gly Glu
            500                 505                 510 ctg ggc gcc cag ccc caa cag gac cat gca cgc tgg ccc cgg ggc agc        1705
Leu Gly Ala Gln Pro Gln Gln Asp His Ala Arg Trp Pro Arg Gly Ser
        515                 520                 525 agc ctg tcc gag tgc agt gag ggg gat gtc acc atg gcc aac acc atg        1753
Ser Leu Ser Glu Cys Ser Glu Gly Asp Val Thr Met Ala Asn Thr Met
    530                 535                 540 gag gag att ctg gaa gag agt gag atc tagggtggag ttccaccacc             1800
```

```
Glu Glu Ile Leu Glu Glu Ser Glu Ile
545                 550 ctggctctgc tcccagggac tcttgagggg gcccaggaag aggaagcaaa gcaggacaca    1860
cgttgctggg cacggaatca ttctcgttcc attcaccatg ccactttgat atgaaagcta    1920
tcacaaggtt cttcaagctc tgtatgaaag aggctgtgtg tcatgctcac agcctctgcc    1980
tgctcttctc atcctaataa ccccaccag tgtgttttcc acaatgccca ccagaccta     2040 gggcctggct ctaaattcaa gccaatgaag tcccacccgg aattcttttg cttttaccc    2100 ctggaagaaa ta                                                       2112

<210> SEQ ID NO 12
<211> LENGTH: 553
<212> TYPE: PRT
<213> ORGANISM: Homo sapiens

<400> SEQUENCE: 12

Met Lys Leu Gly Ser Ser Arg Ala Gly Pro Gly Arg Gly Ser Ala Gly
1               5                   10                  15

Leu Leu Pro Gly Val His Glu Leu Pro Met Gly Ile Pro Ala Pro Trp
            20                  25                  30

Gly Thr Ser Pro Leu Ser Phe His Arg Lys Cys Ser Leu Trp Ala Pro
        35                  40                  45

Gly Arg Pro Phe Leu Thr Leu Val Leu Leu Val Ser Ile Lys Gln Val
    50                  55                  60

Thr Gly Ser Leu Leu Glu Glu Thr Thr Arg Lys Trp Ala Gln Tyr Lys
65                  70                  75                  80

Gln Ala Cys Leu Arg Asp Leu Leu Lys Glu Pro Ser Gly Ile Phe Cys
                85                  90                  95

Asn Gly Thr Phe Asp Gln Tyr Val Cys Trp Pro His Ser Ser Pro Gly
            100                 105                 110

Asn Val Ser Val Pro Cys Pro Ser Tyr Leu Pro Trp Trp Ser Glu Glu
        115                 120                 125

Ser Ser Gly Arg Ala Tyr Arg His Cys Leu Ala Gln Gly Thr Trp Gln
    130                 135                 140

Thr Ile Glu Asn Ala Thr Asp Ile Trp Gln Asp Asp Ser Glu Cys Ser
145                 150                 155                 160

Glu Asn His Ser Phe Lys Gln Asn Val Asp Arg Tyr Ala Leu Leu Ser
                165                 170                 175

Thr Leu Gln Leu Met Tyr Thr Val Gly Tyr Ser Phe Ser Leu Ile Ser
            180                 185                 190

Leu Phe Leu Ala Leu Thr Leu Leu Phe Leu Arg Lys Leu His Cys
        195                 200                 205

Thr Arg Asn Tyr Ile His Met Asn Leu Phe Ala Ser Phe Ile Leu Arg
    210                 215                 220

Thr Leu Ala Val Leu Val Lys Asp Val Phe Tyr Asn Ser Tyr Ser
225                 230                 235                 240

Lys Arg Pro Asp Asn Glu Asn Gly Trp Met Ser Tyr Leu Ser Glu Met
                245                 250                 255

Ser Thr Ser Cys Arg Ser Val Gln Val Leu Leu His Tyr Phe Val Gly
            260                 265                 270

Ala Asn Tyr Leu Trp Leu Leu Val Glu Gly Leu Tyr Leu His Thr Leu
        275                 280                 285

Leu Glu Pro Thr Val Leu Pro Glu Arg Arg Leu Trp Pro Arg Tyr Leu
    290                 295                 300
```

```
Leu Leu Gly Trp Ala Phe Pro Val Leu Phe Val Pro Trp Gly Phe
305                 310                 315                 320

Ala Arg Ala His Leu Glu Asn Thr Gly Cys Trp Thr Thr Asn Gly Asn
            325                 330                 335

Lys Lys Ile Trp Trp Ile Ile Arg Gly Pro Met Met Leu Cys Val Thr
            340                 345                 350

Val Asn Phe Phe Ile Phe Leu Lys Ile Leu Lys Leu Leu Ile Ser Lys
            355                 360                 365

Leu Lys Ala His Gln Met Cys Phe Arg Asp Tyr Lys Tyr Arg Leu Ala
370                 375                 380

Lys Ser Thr Leu Val Leu Ile Pro Leu Leu Gly Val His Glu Ile Leu
385                 390                 395                 400

Phe Ser Phe Ile Thr Asp Asp Gln Val Glu Gly Phe Ala Lys Leu Ile
            405                 410                 415

Arg Leu Phe Ile Gln Leu Thr Leu Ser Ser Phe His Gly Phe Leu Val
            420                 425                 430

Ala Leu Gln Tyr Gly Phe Ala Asn Gly Glu Val Lys Ala Glu Leu Arg
            435                 440                 445

Lys Tyr Trp Val Arg Phe Leu Leu Ala Arg His Ser Gly Cys Arg Ala
450                 455                 460

Cys Val Leu Gly Lys Asp Phe Arg Phe Leu Gly Lys Cys Pro Lys Lys
465                 470                 475                 480

Leu Ser Glu Gly Asp Gly Ala Glu Lys Leu Arg Lys Leu Gln Pro Ser
            485                 490                 495

Leu Asn Ser Gly Arg Leu Leu His Leu Ala Met Arg Gly Leu Gly Glu
            500                 505                 510

Leu Gly Ala Gln Pro Gln Gln Asp His Ala Arg Trp Pro Arg Gly Ser
            515                 520                 525

Ser Leu Ser Glu Cys Ser Glu Gly Asp Val Thr Met Ala Asn Thr Met
530                 535                 540

Glu Glu Ile Leu Glu Glu Ser Glu Ile
545                 550

<210> SEQ ID NO 13
<211> LENGTH: 463
<212> TYPE: PRT
<213> ORGANISM: Rattus norvegicus

<400> SEQUENCE: 13

Met Ala Gly Ala Pro Gly Pro Leu Arg Leu Ala Leu Leu Leu Leu Gly
1               5                   10                  15

Met Val Gly Arg Ala Gly Pro Arg Pro Gln Gly Ala Thr Val Ser Leu
            20                  25                  30

Trp Glu Thr Val Gln Lys Trp Arg Glu Tyr Arg Arg Gln Cys Gln Arg
        35                  40                  45

Ser Leu Thr Glu Asp Pro Pro Ala Thr Asp Leu Phe Cys Asn Arg
    50                  55                  60

Thr Phe Asp Glu Tyr Ala Cys Trp Pro Asp Gly Glu Pro Gly Ser Phe
65                  70                  75                  80

Val Asn Val Ser Cys Pro Trp Tyr Leu Pro Trp Ala Ser Ser Val Pro
            85                  90                  95

Gln Gly His Val Tyr Arg Phe Cys Thr Ala Glu Gly Leu Trp Leu Gln
            100                 105                 110

Lys Asp Asn Ser Ser Leu Pro Trp Arg Asp Leu Ser Glu Cys Glu Glu
```

```
            115                 120                 125
Ser Lys Arg Gly Glu Arg Ser Arg Glu Gln Leu Leu Phe Leu
    130                 135                 140

Tyr Ile Ile Tyr Thr Val Gly Tyr Ala Leu Ser Phe Ser Ala Leu Val
145                 150                 155                 160

Ile Ala Ser Ala Ile Leu Leu Gly Phe Arg His Leu His Cys Thr Arg
                165                 170                 175

Asn Tyr Ile His Leu Asn Leu Phe Ala Ser Phe Ile Leu Arg Ala Leu
            180                 185                 190

Ser Val Phe Ile Lys Asp Ala Ala Leu Lys Trp Met Tyr Ser Thr Ala
        195                 200                 205

Ala Gln Gln His Gln Trp Asp Gly Leu Leu Ser Tyr Gln Asp Ser Leu
    210                 215                 220

Ser Cys Arg Leu Val Phe Leu Leu Met Gln Tyr Cys Val Ala Ala Asn
225                 230                 235                 240

Tyr Tyr Trp Leu Leu Val Glu Gly Val Tyr Leu Tyr Thr Leu Leu Ala
                245                 250                 255

Phe Ser Val Phe Ser Glu Gln Trp Ile Phe Arg Leu Tyr Val Ser Ile
            260                 265                 270

Gly Trp Gly Val Pro Leu Leu Phe Val Val Pro Trp Gly Ile Val Lys
        275                 280                 285

Tyr Leu Tyr Glu Asp Glu Gly Cys Trp Thr Arg Asn Ser Asn Met Asn
    290                 295                 300

Tyr Trp Leu Ile Ile Arg Leu Pro Ile Leu Phe Ala Ile Gly Val Asn
305                 310                 315                 320

Phe Leu Ile Phe Val Arg Val Ile Cys Ile Val Val Ser Lys Leu Lys
                325                 330                 335

Ala Asn Leu Met Cys Lys Thr Asp Ile Lys Cys Arg Leu Ala Lys Ser
            340                 345                 350

Thr Leu Thr Leu Ile Pro Leu Leu Gly Thr His Glu Val Ile Phe Ala
        355                 360                 365

Phe Val Met Asp Glu His Ala Arg Gly Thr Leu Arg Phe Ile Lys Leu
    370                 375                 380

Phe Thr Glu Leu Ser Phe Thr Ser Phe Gln Gly Leu Met Val Ala Ile
385                 390                 395                 400

Leu Tyr Cys Phe Val Asn Asn Glu Val Gln Leu Glu Phe Arg Lys Ser
                405                 410                 415

Trp Glu Arg Trp Arg Leu Glu His Leu His Ile Gln Arg Asp Ser Ser
            420                 425                 430

Met Lys Pro Leu Lys Cys Pro Thr Ser Ser Leu Ser Ser Gly Ala Thr
        435                 440                 445

Ala Gly Ser Ser Met Tyr Thr Ala Thr Cys Gln Ala Ser Cys Ser
    450                 455                 460

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aacccactgc ttac                                                        14
```

-continued

```
<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cccagaatag aatgacacc                                                    19

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16 cagggccgg tacctctcca ctcc                                               24

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ttgggtcctc gagtggccaa gctgcg                                            26

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gggtagtcgg tacctctaga gcaagttcag cc                                     32

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ataacagagg atcctcgagt atttcttcca g                                      31

<210> SEQ ID NO 20
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
acaggcatgt ctggaagact tactcaagga accttctggc at                          42

<210> SEQ ID NO 21
```

```
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
atgccagaag gttccttgag taagtcttcc agacatgcct gt                              42

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ttcctctgtg gtaccaagag gaatgc                                               26

<210> SEQ ID NO 23
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggtggactcg aggtaccgat ctcactctct tccagaatc                                 39

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gtggagagga tttgtgcaaa catttc                                               26

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agagacattt ccaggagaag aatgag                                               26

<210> SEQ ID NO 26
<211> LENGTH: 15
<212> TYPE: PRT
<213> ORGANISM: Rattus norvegicus

<400> SEQUENCE: 26

Gln Thr Arg Glu Asn Thr Thr Asp Ile Trp Gln Asp Glu Ser Glu
 1               5                  10                  15

<210> SEQ ID NO 27
<211> LENGTH: 13
<212> TYPE: PRT
<213> ORGANISM: Rattus norvegicus
```

```
<400> SEQUENCE: 27

Ser Glu Gly Asp Gly Ser Glu Thr Leu Gln Lys Leu Arg
  1               5                  10

<210> SEQ ID NO 28
<211> LENGTH: 14
<212> TYPE: PRT
<213> ORGANISM: Rattus norvegicus

<400> SEQUENCE: 28

Ser His Asn Ser Tyr Ser Lys Arg Pro Asp Asp Glu Ser Gly
  1               5                  10
```

US 7,473,537 B1

CLONED GLUCAGON-LIKE PEPTIDE-2 RECEPTORS

This application is a national stage entry of PCT international application no. PCT/CA97/00969, filed Dec. 15, 1997, which claims priority to U.S. patent application Ser. No. 08/845,546, filed Apr. 24, 1997, issued as U.S. Pat. No.: 6,077,949; U.S. patent application Ser. No. 08/767,224, filed Dec. 13, 1996 and U.S. patent application Ser. No. 08/787,721, filed Jan. 24, 1997.

FIELD OF THE INVENTION

The invention is in the field of molecular biology. It relates, more particularly, to cloned glucagon-like peptide 2 receptors and their use in drug screening and related applications.

BACKGROUND OF THE INVENTION

Glucagon-like peptide-2 (GLP-2) is a 33 amino acid peptide, which is expressed in a tissue determined fashion from the pleiotrophic glucagon gene and is highly related in terms of amino acid sequence to glucagon and Glucagon-like peptide-1 (GLP-1). Mammalian forms of GLP-2 are highly conserved: for example, the human and degu (a south American rodent) forms differ by one and three amino acids respectively from rat GLP-2. Recently it was demonstrated that GLP-2 is an intestinotrophic peptide hormone; when given exogenously, GLP-2 can produce a marked increase in the proliferation of small intestinal epithelium of the test mice (Drucker et al, (1996) PNAS, 93:7911-7961). More recently, GLP-2 has been shown to increase D-Glucose maximal transport rate across the intestinal basolateral membrane (Cheeseman and Tseng: American Journal of Physiology (1996) 271: G477-G482).

To accelerate research into gastrointestinal biology and development of drugs useful in the treatment of various medial conditions including gastrointestinal disorders, it would be useful to provide the receptor through which the effects of GLP-2 are mediated.

SUMMARY OF THE INVENTION

The GLP-2 receptor has now been cloned and characterized. Accordingly, the present invention provides an isolated polynucleotide encoding a GLP-2 receptor, particularly including mammalian forms and homologs thereof such as, in specific embodiments, the rat and human forms. In aspects of the invention, polynucleotide coding for a GLP-2 receptor is utilized for expression to obtain functional receptor protein and, in optionally labelled form, for further gene cloning to identify structurally related receptor proteins. In related aspects of the invention, anti-sense versions of GLP-2 receptor-encoding polynucleotides and fragments thereof are obtained and utilized to regulate GLP-2 receptor expression.

In another of its aspects, the invention provides GLP-2 receptor as a product of recombinant production in a cellular host. In related aspects, there are provided recombinant host cells that express GLP-2 receptor, as well as receptor-bearing membranes derived from such cells, and expression constructs in which polynucleotide coding for the GLP-2 receptor is linked in expression controls functional in the selected host cell.

In another of its aspects, the GLP-2 receptor is utilized in a chemicals screening program to identify GLP-2 receptor ligands. This method comprises the steps of incubating the candidate ligand with a GLP-2 receptor-producing cell of the present invention, or with a membrane preparation derived therefrom, and then measuring whether, or the extent to which, binding has occurred. Using cells that express a GLP-2 receptor coupled functionally to a second messenger system, such binding can be determined indirectly, to reveal ligand against activity, by detecting an appropriate reporter.

In another of its aspects, the invention provides antibodies directed to the GLP-2 receptor, for use for example in diagnostic procedures.

The invention is further described with reference to the following drawings in which:

BRIEF REFERENCE TO THE DRAWINGS

FIG. 1 discloses a cDNA sequence (SEQ ID NO: 1), nucleotides 137-1789 of which encode the rate GLP-2 receptor wherein ambiguous base pairs are indicated using the standard IUB nomemenclature (R: A or G, Y: C or T, M: A or C, K: G or T, S: G or C, W: A or T).

FIG. 2 discloses the amino acid sequence of the expression product (SEQ ID NO: 2) from the cDNA of FIG. 1.

FIG. 3 illustrates the relative potencies of GLP-2 peptide and GLP-1 peptide for the receptor encoded by SEQ ID NO: 1.

FIG. 4 discloses a cDNA sequence of 667 nucleotides (SEQ ID NO: 9) which encodes a 222 amino acid fragment (SEQ ID NO: 10) of a human GLP-2 receptor.

FIG. 5 discloses the amino acid sequence (SEQ ID NO: 10) expressed from the cDNA (SEQ ID NO: 9) of FIG. 4.

FIG. 6 discloses a cDNA sequence (SEQ ID NO: 11), nucleotides 121-1779 of which encode a human GLP-2 receptor (SEQ ID NO: 12).

FIG. 7 discloses the amino acid sequence of the expression product (SEQ ID NO: 12) from the cDNA of FIG. 6.

Figure 8:
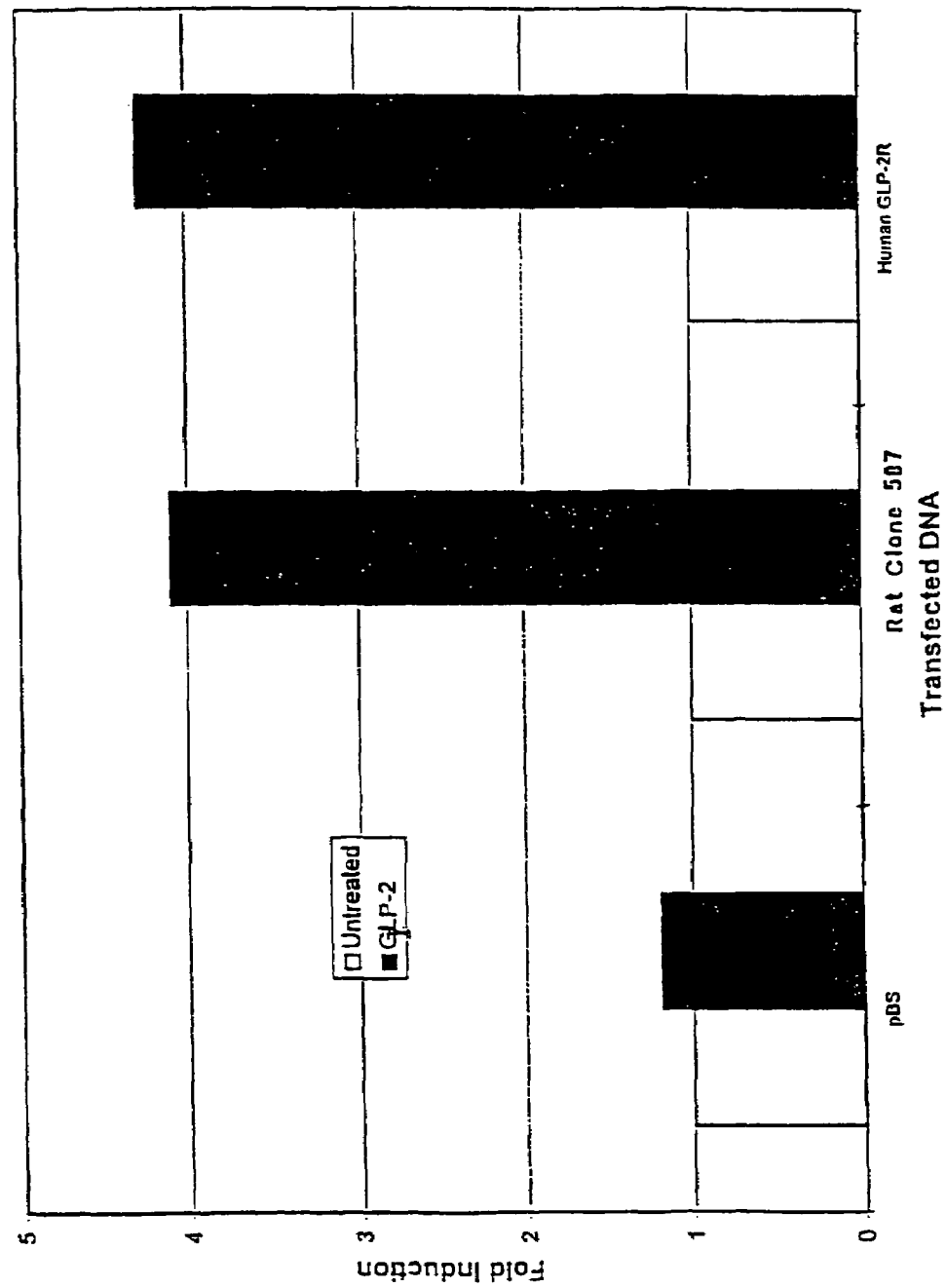

FIG. 8 illustrates the functional activation by GLP-2 peptide of the human receptor encoded by SEQ ID NO: 11 (FIG. 8).

FIG. 9 compares the amino acid sequences of the rat GLP-2 receptor (SEQ ID NO: 2) and the human GLP-2 receptor (SEQ ID NO: 12).

FIG. 10 compares the amino acid sequences of the rat GLP-2 receptor (SEQ ID NO: 2) and the human GLP-2 receptor (SEQ ID NO: 12) against rat GLP-1 receptor (SEQ ID NO: 13).

DETAILED DESCRIPTION AND PREFERRED EMBODIMENTS

The invention relates in one respect to polynucleotides, in their isolated form, that code the GLP-2 receptors. As used herein "isolated" means separated from polynucleotides that encode other proteins. In the context of polynucleotide libraries, for instance, GLP-2 receptor-encoding polynucleotide is considered "isolated" when it has been selected, and hence removed from association with other polynucleotides within the library. Such polynucleotides may be in the form of RNA, or in the form of DNA including cDNA, genomic DNA and synthetic DNA. The GLP-2 receptors are characterized by structural features common to the G-protein coupled receptor class, including seven transmembrane regions, and by the functional properties of binding GLP-2 peptide selectively, i.e., preferentially, to GLP-1 peptide. Such selective binding is revealed as a statistically significant greater binding affinity of GLP-2 then of GLP-1, in the context of the assay chosen to measure such affinity. When expressed functionally in a host cell, i.e., in operable linkage with a responsive second messenger system the GLP-2 receptors are capable further of responding to GLP-2 binding by signal transduction. In this regard, the activity of a G-protein coupled receptor such as a GLP-2 receptor can be measured using any of a variety of appropriate functional assays in which activation of the receptor results in detectable change in the level of some second messenger system, such as adenylate cyclase, calcium mobilization, inositol phospholipid hydrolysis products or guanylyl cyclase.

With reference to FIG. 9 and FIG. 10, which reveals homologies across amino acid sequences representing human and rat GLP-2 receptors, regions of 100% identity are indicated by solid vertical bars. In embodiments of the invention, the GLP-2 receptors are defined structurally as receptors that incorporate these regions of amino acid sequence and that also exhibit the functional characteristic of binding GLP-2 peptide selectively, relative to GLP-1 peptide. In more specific embodiments, the GLP-2 receptor structure further incorporates those amino acids which, across the human and rat receptor species, are highly conserved (indicated by ':'). At these sites, it will be appreciated that the sequence can contain any amino acid within the highly conserved amino acid family to which the identified amino acid belongs. In still more specific embodiments, the GLP-2 receptor have a structure which still further incorporates to the moderatively conserved amino acids (indicated by '.') meaning, at these sites, that the amino acids within the moderately conserved family to which they belong. Beyond these sequences, the GLP-2 receptor structure can vary widely in embodiments of the invention, in allowing for non-conservative amino acid substitutions.

In one embodiment of the invention, the GLP-2 receptor is a rat GLP-2 receptor having the amino acid sequence of SEQ ID NO: 2. In a specific embodiment of the invention, this rat GLP-2 receptor is encoded by the polynucleotide sequence of SEQ ID NO: 1. This particular GLP-2 receptor-encoding polynucleotide, also referred to as the WBR gene, is a cDNA of rat origin. The expression product of this polynucleotide incorporates the mature form of the GLP-2 receptor, and additionally incorporates a secretion signal that is removed before membrane integration of the mature GLP-2 receptor product. Such a signal sequence may be naturally present on the polypeptides or replaced with a functionally equivalent secretion signal which is heterologous to the GLP-2 receptor. The replacement secretion signal chosen will depend on the expression system being used and will typically, but not essentially be endogenous to the chosen host and, also typically but not essentially, be homologous to the chosen expression controlling sequences.

The expressed rat GLP-2 receptor product (FIG. 2, SEQ ID NO: 2) is characterized structurally as a single 550 amino acid polypeptide chain having a predicted molecular weight of 72 kDa. Two functional translation start sites of the rat GLP-2 receptor have been identified, these are the codons encoding methionine 1 and methionine 42 of SEQ ID NO: 2. Without wishing to be limited, by analogy with the GLP-1 receptor, it is believed that residues 1-66 of SEQ ID NO: 2 are cleaved to provide a mature protein (i.e., the amino acid sequence of the receptor as it appears in the cell membrane) of 484 amino acids. With respect to structural domains of this GLP-2 receptor, hydropathy analysis and sequence alignment with related members of this sub-family of G protein coupled receptors indicates seven putative transmembrane domains, one spanning residues 181-203 inclusive (TM I), another spanning residues 211-230 (TM II), a third spanning residues 262-285 (TM III), a fourth spanning residues 300-321 (TM VI), a fifth spanning 339-362 (TM V), a sixth spanning 386-405 (TM VI) and a seventh spanning 422-441 (TM VII). Based on this assignment, it is likely that this GLP-2 receptor, in its natural membrane-bound form, consists of a an N-terminal extracellular domain, followed by a hydrophobic region containing seven transmembrane domains and an intracellular 442-550 amino acid C-terminal domain. The protein exhibits the highest degree of homology to the rat GLP-1 receptor with 49% identity at the amino acid level.

In a related embodiment, the GLP-2 receptor is of human origin (SEQ ID NO: 9) and incorporates the human GLP-2 receptor fragment having the amino acids of SEQ ID NO: 10.

This polynucleotide was isolated using the rat cDNA sequence as generally described below and as detailed in Example 3. In a further related embodiment of the invention, the cDNA is of human origin (SEQ ID NO: 11) and encodes the full length human GLP-2 receptor having residues 67-533 of the amino acid sequence of SEQ ID NO: 12. The human GLP-2 receptor precursor product (FIG. 7, SEQ ID NO: 12) is characterized structurally as a single 553 amino acid polypeptides chain having a predicted molecular weight of 72 kDa. It is believed that, as for the rat GLP-2 receptor, this sequence, this precursor form of the human GLP-2 receptor incorporates an N-terminal signal sequence, which can be replaced by a functionally equivalent heterologous signal sequence. Without wishing to be limited it is believed that the mature form of the human GLP-2 receptor results after cleavage of residues 1-66 of SEQ ID NO: 12 (FIG. 7). With respect to structural domains of this GLP-2 receptor, hydropathy analysis and sequence alignment with related members of this sub-family of G protein coupled receptors indicates seven putative transmembrane domains, one spanning residues 181-203 inclusive (TM I), another spanning residues 211-230 (TM II), a third spanning residues 262-285 (TM III), a fourth spanning residues 300-321 (TM IV), a fifth spanning residues 339-362 (TM V), a sixth spanning residues 386-405 (TM VI), and a seventh spanning residues 422-441 (TM VII). Based on this assignment, it is likely that this GLP-2 receptor, in its natural membrane-bound form, consist of an N-terminal extracellular domain, followed by a hydrophobic region containing seven transmembrane domains interspaced with six short hydrophillic domains, and an intracellular domain, which is predicted to span residues 442-553. A second form of this GLP-2 receptor encompassed by the invention has a translational start site at the methionine codon at position 26 of the amino acid sequence presented in FIG. 7 SEQ ID NO: 12. The resulting 528 amino acid polypeptide chain also consists of an extracellular domain, seven transmembrane domains, and a C-terminal intracellular domain, and is at least 95% identical in sequence to residues 26-553 of the sequence presented in FIG. 7, SEQ ID NO: 12.

In another embodiment, the invention provides GLP-2 receptor polynucleotide sequences and their unique sequence fragments as a tool useful to identify and isolate structurally related polynucleotides. At low stringency hybridization conditions, for instance, polynucleotide libraries can be probed to identify genes that are at least about 50% homologous to the GLP-2 receptor gene. To facilitate isolation of rat GLP-2 receptor gene homologs that are also GLP-2 receptor-encoding, stringency conditions are desirably enhanced to identify homologs having at least 80% (medium stringency) sequence identity homology at the polynucleotide level to receptor gene. More desirably the WBR gene homologs are 90% identical, (high stringency) and most desirably they have at least 95% sequence (high stringency) identity when compared to WBR. Preferably, the isolated WBR homologs are characterized in that (1) they can be amplified using the PCR primers of SEQ ID NO: 3 and SEQ ID NO: 4 and (2) they bind to the probe of SEQ ID NO: 5 under high stringency conditions.

Still more preferably, the isolated homologs are those which bind, under conditions of high stringency, with consensus regions of the GLP-2 receptor-encoding polynucleotides, i.e., those regions of the rat and human GLP-2 receptor-encoding polynucleotides which are identical and, relative to GLP-1 receptor-encoding sequences, are also unique to the GLP-2 receptor-encoding polynucleotides. Alignment of this nature reveals a number consensus regions for GLP-2: for example nucleotides spanning from 1460-1786. In one embodiment of the invention, these sequences, and their complements, constitute polynucleotide fragments useful, as just described for the intact gene, to identify polynucleotides structurally related to the human and rat GLP-2 receptor embodiments of the invention.

In a related embodiment, the cDNA sequence or the unique fragments of the GLP-2 receptor, most preferably of the human GLP-2 receptor, can be used in appropriately labelled form, e.g., $p^{32}$ labelled, for diagnosis of conditions associated with aberrant expression of the GLP-2 receptor. For example, over or under expression or expression in an inappropriate tissue. In one embodiment appropriate PCR primers (e.g., regions unique to the GLP-2 receptor but conserved between species) can be used diagnostically to identify aberrant structure or levels of GLP-2 receptor mRNA, e.g., associated with inherited or acquired disease states.

It has been found that the human GLP-2 receptor is located on chromosome 17P13. Thus, in a further embodiment, the invention provides expression products from this locus that hybridize with the human GLP-2 receptor polynucleotide (FIG. 6; SEQ ID NO: 11) under stringent conditions.

As source material to isolate GLP-2 receptor-encoding homologs of the rat GLP-2 receptor-encoding polynucleotide gene, it is desirable but not necessary to use libraries of fetal or mature hypothalamal, jejunal, hindbrain or stomach tissue obtained from the vertebrate species targeted for receptor isolation. The invention accordingly includes not only the rat GLP-2 receptor-encoding polynucleotide of SEQ ID NO: 1, but structural homologs thereof and particularly those that code for proteins having GLP-2 receptor properties. As exemplified hereinbelow, the WBR gene has been used successfully as a starting material to clone the human homolog of the rat GLP-2 receptor. Thus, the invention provides polynucleotides that encode GLP-2 receptors, including rat GLP-2 receptor and vertebrate homologs, particularly mammalian homologs thereof including human homologs, as well as synthetic variants of these.

It will be appreciated that such homologs can also be identified in libraries by screening, as noted, with fragments of the rat receptor gene or the human homolog, which incorporate at least 15 nucleotides, and preferably at least 25 nucleotides. With reference to SEQ ID NO: 1 and the nucleotide numbering appearing thereon, suitable nucleotide fragments include in addition to the consensus nucleotide fragments noted above, those corresponding in sequence to the extracellular GLP-2 binding domain, and the stipulated transmembrane regions and the C-terminal portion of the receptor.

Technically, the identification of GLP-2 receptor genes can be achieved by applying standard hybridization or amplification techniques to a tissue-derived polynucleotide library. A wide variety of such libraries are commercially available. Where construction of a cDNA library is necessary, established techniques are applied. For example, isolation of such a WBR homolog typically will entail extraction of total messenger RNA from a fresh source of tissue, such as hypothalamal, jejunal, stomach or hindbrain tissue, preferably hypothalamal tissue or cell lines derived from these tissues, followed by conversion of message to cDNA and formation of a library in for example a bacterial plasmid, more typically a bacteriophage.

Such bacteriophage harboring fragments of the DNA are typically grown by plating on a lawn of susceptible *E. coli* bacteria, such that individual phage plaques or colonies can be isolated. The DNA carried by the phage colony is then typically immobilized on a nitro-cellulose or nylon-based hybridization membrane, and then hybridized, under carefully controlled conditions, to a radioactively (or otherwise) labelled probe sequence to identify the particular phage colony carrying the fragment of DNA of particular interest, in this case a rat or human GLP-2 homolog. The phage carrying the particular gene of interest is then purified away from all other phages from the library, in order that the foreign gene may be more easily characterized. Typically, the gene or a portion thereof is then isolated by subcloning into a plasmatic vector for convenience, especially with respect to the full determination of its DNA sequence.

As an alternative to obtaining GLP-2 encoding DNA directly as a DNA insert from an available or a constructed cDNA library, in light of the present disclosure it can be synthesized de novo using established techniques of gene synthesis. Because of the length of the GLP-2 receptor-encoding DNAs of SEQ ID NO: 1, SEQ ID NO: 9 and SEQ ID NO: 11, application of automated synthesis may required staged gene construction, in which regions of the gene up to about 300 nucleotides in length are synthesized individually and then ligated in correct succession for final assembly. Individually synthesized gene regions can be amplified by PCR. The application of automated synthesis may typically be applied by synthesizing specific regions or fragments of the gene and ligating them, usually via designed overlaps, in correct succession to form the final gene sequence. In this case, the longer the oligonucleotide building blocks, the fewer will be the ligations needed, resulting in greater ease of assembly.

The application of automated gene synthesis techniques provides an opportunity for generating sequence variants of the naturally occurring GLP-2 receptor gene. It will be appreciated, for example, that polynucleotides coding for the GLP-2 receptor herein described can be generated by substituting one or more synonymous codons for those represented in the naturally occurring polynucleotide sequences herein provided and such “synonymous codon equivalents” are within the scope of the present invention. In addition, polynucleotides coding for synthetic variants of the GLP-2 receptor herein provided can be generated which incorporate from 1 to 20, e.g., from 1 to 5, amino acid substitutions, or deletions or additions. Preferred sites for such a modification include areas of non homology between the rat and human sequence, for example amino acid ranges 70-92, 328-350 and 475-504. Since it will be desirable typically to retain the natural ligand binding profile of the receptor for screening purposes, it is desirable to limit amino acid substitutions, for example to the so-called conservative replacements in which amino acids of similar charge are substituted (FIG. 9), and to limit substitutions to those sites less critical for receptor activity. For example, substitution of nucleotides “G” and “A” for nucleotides “A” and “G” respectively at positions 374 and 375 of the human cDNA sequence of SEQ ID NO: 11; resulting in the replacement of the naturally occurring arginine residue at position 85 of SEQ ID NO: 12 with a glutamic acid residue, provides a functional receptor. This functional receptor is referred to herein as the $Glu^{85}$ variant human GLP-2 receptor.

Having obtained GLP-2 receptor encoding polynucleotide, GLP-2 receptor can be produced in a number of ways, including in vitro transcription and via incorporation of the DNA into a suitable expression vector and expression in the appropriate host, for example in a bacterium such as E. coli, in yeast or in insect or in a mammalian cell. A variety of gene expression systems have been adapted for use with these hosts and are now commercially available, and any one of these systems can be selected to drive expression of the GLP-2 receptor-encoding DNA. Expression vectors may be selected to provide transformed cell lines that express the receptor-encoding DNA either transiently or in a stable manner. For transient expression, host cells are typically transformed with an expression vector harboring an origin of replication functional in a mammalian cell. For stable expression, such replication origins are unnecessary, but the vectors will typically harbor a gene coding for a product that confers on the transformants a survival advantage, to enable their selection such as a gene coding for neomycin resistance in which case the transformants are plated in medium supplemented with neomycin.

These expression systems, available typically but not exclusively in the form of plasmidic vectors, incorporate expression cassettes the functional components of which include DNA constituting expression controlling sequences and optionally also signal peptides encoding sequences, which are host-recognized and enable expression of the receptor-encoding DNA when linked 5' thereof. The systems further incorporate DNA sequences which terminate expression when linked 3' of the receptor-encoding region. Thus, for expression in the selected mammalian cell host, there is generated a recombinant DNA expression construct in which the receptor-encoding DNA is linked with expression controlling DNA sequences recognized by the host, and which include a region 5' of the receptor-encoding DNA to drive expression, and a 3' region to terminate expression.

Included among the various recombinant DNA expression systems that can be used to achieve mammalian cell expression of the receptor-encoding DNA are those that exploit promoters of viruses that infect mammalian cells, such as the promoter from the cytomegalovirus (CMV), the Rous sarcoma virus (RSV), simian virus (SV40), murine mammary tumor virus (MMTV) and others. Also useful to drive expression are promoters such as the LTR of retroviruses, insect cell promoters such as those regulated by temperature, and isolated from Drospophila, as well as mammalian gene promoters such as those regulated by heavy metals i.e. the metallothionein gene promoter, and other steroid-inducible promoters.

In another of its aspects, the invention provides cells or membranes derived therefrom which are adapted by genetic alteration for use, for example, in identifying GLP-2 receptor ligands. In preferred embodiments, such cells are adapted genetically by the insertion of polynucleotide coding for a GLP-2 receptor. In particularly preferred embodiments, such cells incorporate a recombinant DNA molecule, e.g. an expression construct/vector, in which DNA coding for the GLP-2 receptor and expression controlling elements functional in the host are linked operably to drive expression of the DNA. For incorporation of receptor into cell plasma membranes, the vector can, if desired, be designed to provide a suitable heterologous signal peptide sequence to substitute for the signal peptide encoded naturally within the receptor DNA.

Suitable GLP-2 producing cells include the Chinese hamster ovary (CHO) cells for example of K1 lineage (ATCC CCL 61) including the Pro5 variant (ATCC CRL 1281); the fibroblast-like cells derived from SV40-transformed African Green monkey kidney of the CV-1 lineage (ATCC CCL 70), of the COS-1 lineage (ATCC CRL 1650) and of the COS-7 lineage (ATCC CRL 1651); murine L-cells, murine 3T3 cells (ATCC CRL 1658), murine C127 cells, human embryonic kidney cells of the 293 lineage (ATCC CRL 1573), human carcinoma cells including those of the HeLa lineage (ATCC CCL 2), and neuroblastoma cells of the lines IMR-32 (ATCC CCL 127), SK-N-MC (ATCC HTB 10) and SK-N-SH (ATCC HTB 11).

For use in ligand screening assays, cell lines expressing the receptor-encoding DNA can be stored frozen for later use. Such assays may be performed either with intact cells, or with membrane preparations derived from such cells. The membrane preparations typically provide a more convenient substrate for the ligand binding experiments, and are therefore preferred as binding substrates. To prepared membrane preparations for screening purpose, i.e., ligand binding experiments, frozen intact cells are homogenized while in cold water suspension and a membrane pellet is collected after centrifugation. The pellet is then washed in cold water, and dialyzed to remove any endogenous GLP-2 receptor ligands that would otherwise compete for binding in the assays. The dialyzed membranes may then be used as such, or after storage in lyophilized form, in the ligand binding assays.

The binding of a candidate ligand to a selected GLP-2 receptor of the invention can be assessed typically using a predetermined amount of cell-derived membrane (measured for example by protein determination), generally from about 25 µg to 100 µg. Generally, competitive binding assays will be useful to evaluate the affinity of a test compound relative to GLP-2. This competitive binding assay is performed by incubating the membrane preparation with radiolabelled GLP-2 peptide, for example [$H^3$] or a radioiodinated GLP-2 analog, in the presence of unlabelled test compound added at varying concentrations. Following incubation, either displaced or bound radiolabelled GLP-2 can be recovered and measured, to determine the relative binding affinities of the test compound and GLP-2 for the GLP-2 receptor used as substrate. In this way, the affinities of various compounds for the GLP-2 receptor can be measured.

Alteratively, binding of a candidate ligand to a GLP-2 receptor can be assessed using a functional assay. Using this approach, for example, intact cells harvested about two days following transient transfection or after about the same period following plating of stably transfected cells can be used to assess ligand binding. In a preferred embodiment, 293 EBNA cells (Invitrogen Cat. R620-07) are stably transformed with the pREP7 vector (Invitrogen Cat. V007-50) incorporating expressibly therein a GLP-2 receptor. Thereafter, binding of an agonist (or using a competition base format an antagonist) to the receptor can be discerned by measuring the level of intracellular cAMP. Most conventionally, intracellular cAMP is measured indirectly using a reporter system, wherein an easily measurable and preferably easily quantifiable downstream event indicates the level of intracellular cAMP. For example, measuring the level of the expression of a reporter gene construct having polynucleotide sequence under the control of a promoter which is responsive to cAMP. Alternatively, measurement of intracellular calcium, released from intracellular stores in response to an increase in intracellular cAMP, can be used as an indicator of the level of intracellular cAMP, for example, by incorporating into the transformed cell a protein that fluorescences on binding to calcium. In a preferred embodiment, intracellular cAMP levels are measured using the commercially available EIA kit. An additional advantage of the functionally based approach to assessing ligand binding is that the system can be automated allowing high throughput and ultra high through screening of vast chemical libraries.

As an alternative to using cells that express receptor-encoding DNA, ligand characterization may also be performed using cells for example Xenopus oocytes, that yield functional membrane-bound receptor following introduction of messenger RNA coding for the GLP-2 receptor. In this case, the GLP-2 receptor-encoding polynucleotide of the invention is typically subcloned into a plasmidic vector such that the introduced gene may be easily transcribed into RNA via an adjacent RNA transcription promoter supplied by the plasmidic vector, for example the T3 or T7 bacteriophage promotes. RNA is then transcribed from the inserted gene in vitro, and can then be injected into Xenopus oocytes. Each oocyte is a single cell, but is large enough to be penetrated by a fine-tipped microneedle without causing irreparable damage. Following the injection of nL volumes of an RNA solution, the oocytes are left to incubate for up to several days, whereupon the oocytes are tested for the ability to respond to a particular ligand molecule supplied in a bathing solution.

Candidate GLP-2 receptor ligands can vary widely in structure, and most suitably include proteins which are highly related to GLP-2 itself in terms of amino acid sequence. For instance, the peptide disclosed in co-pending U.S. patent applications WO97/39031 and WO96/32414, incorporated herein by reference, may usefully be screened for GLP-2 receptor binding activity.

In addition to naturally occurring GLP-2 receptor sequences functional chimeric, receptors, incorporating portions of the GLP-2 receptor sequence and the polynucleotides encoding them are also embodiments of the invention. Functional chimeric GLP-2 receptors are constructed by combining the extracellular receptive sequences of a GLP-2 receptor with one or more of the transmembrane and intracellular segments of a known seven transmembrane G-protein coupled receptor for test purposes. This concept was demonstrated by Kobilka et al. (1988, Science 240:1310-1316) who created a series of chimeric α2-β2 adrenergic receptors (AR) by inserting progressively greater amounts of α2-AR transmembrane sequence into β2-AR. The binding activity of known agonists changed as the molecule shifted from having more α2 then β2 conformation, and intermediate constructs demonstrated mixed specificity. The specificity for binding antagonists, however, correlated with the source of the transmembrane domain VII. The importance of transmembrane domain VII for ligand recognition was also found in chimeras utilizing two yeast α-factor receptors and is significant because the yeast receptors are classified as miscellaneous receptors. Thus, functional role of specific domains appears to be preserved throughout the seven transmembrane G-protein coupled receptor family regardless of category.

In parallel fashion, internal segments or cytoplasmic domains from a particular GLP-2 receptor are exchanged with the analogs domains of a known seven transmembrane G-protein coupled receptor and used to identify the structural determinants responsible for coupling the receptors to trimeric G-proteins (Dohlman et al. (1991) Annu Rev Biochem 60:653-688). A chimeric receptor in which domains V, VI, and the intracellular connecting loop from β2-AR were substituted into a2-AR was shown to bind ligands with a2-AR specificity, but to stimulate adenylate cyclase in the manner of β2-AR. This demonstrates that for adrenergic-type receptors, G-protein recognition is present in domains V and VI and their connecting loop. The opposite situation was predicted and observed for a chimera in which the V→VI loop from α1-AR replaced the corresponding domain on β2-AR and the resulting receptor bound ligands with β2-AR specificity and activated G-protein-mediated phosphatidylinositol turnover in the α1-AR manner. Finally, chimeras constructed from muscarinic receptors also demonstrated that V→VI loop is the major determinant for specificity of G-protein activity.

Chimeric or modified seven transmembrane G-protein coupled receptors containing substitutions in the extracellular and transmembrane regions have shows that these portions of the receptor determine ligand binding specificity. For example, two Ser residues conserved in domain V of all adrenergic and D catecholamine receptors are necessary for potent agonist activity. These serines are believed to form hydrogen bonds with the catechol moiety of the agonists within the binding site. Similarly, an Asp residue present in domain III of all seven transmembrane G-protein coupled receptors which bind biogenic amines is believed to form an ion pair with the ligand amine group in the binding site.

Functional, cloned seven transmembrane G-protein coupled receptors are expressed in heterologous expression systems and their biological activity assessed (e.g., Marullo et al. (1988) Proc Natl Acad Sci 85:7551-7555; King et al. (1990) Science 250:121-123). One heterologous system introduces genes for a mammalian seven transmembrane G-protein coupled receptors and a mammalian G-protein into yeast cells. The seven transmembrane G-protein coupled receptor is shown to have appropriate ligand specificity and affinity and trigger appropriate biological activation—growth arrest and morphological changes—of the yeast cells.

An alternate procedure for testing chimeric receptors is based on the procedure utilizing the $P_{2u}$ purinergic receptor ($P_{2u}$) as published by Erb et al. (1993, Proc Natl Acad Sci 90:104411-104453). Function is easily tested in cultured K562 human leukaemia cells because these cells lack $P_{2u}$ receptors. K562 cells are transfected with expression vectors containing either normal or chimeric $P_{2u}$ and loaded with fura-a, fluorescent probe for Ca++. Activation of properly assembled and functional $P_{2u}$ receptors with extracellular UTP or ATP mobilizes intracellular Ca++ which reacts with fura-a and is measured spectrofluormetrically. As with the seven transmembrane G-protein coupled receptors above, chimeric genes are created by combining sequences for extracellular receptive segments or any newly discovered seven transmembrane G-protein coupled receptors polypeptide with the nucleotides for the transmembrane and intracellular segments of the known $P_{2u}$ molecule. Bathing the transfected K562 cells in microwells containing appropriate ligands triggers binding and fluorescent activity defining effectors of the seven transmembrane G-protein coupled receptors molecule. Once ligand and function are established, the $P_{2u}$ system is useful for defining antagonists or inhibitors which block binding and prevent such fluorescent reactions.

In addition to using the receptor-encoding DNA to construct cell lines useful for ligand screening, expression of the DNA can according to another aspect of the invention be performed to produce fragments of the receptor in soluble form, for structure investigation, to raise antibodies and for other experimental uses. It is expected that the extracellular portion of the GLP-2 receptor contributes significantly to the binding of ligand molecule. It is therefore desirable in the first instance to facilitate the characterization of the receptor-ligand interaction by providing this extracellular ligand-binding domain in quantity and in isolated form, i.e., free from the remainder of the receptor. Such as construct has been made for the rat GLP-1 receptor, and it was shown to bind GLP-1 (Wilmen et al. (1996) FEBS LETTS, 398:43-47).

To accomplish this, the full-length GLP-2 receptor-encoding DNA may be modified by site-directed mutagenesis, so as to introduce a translational stop codon into the extracellular N-terminal region, immediately before the sequence encoding the first transmembrane domain (TMI), i.e., before residue 181 of SEQ ID NO: 2 and before residue 181 of SEQ ID NO: 12. Since there will no longer be produced any transmembrane domain(s) to "anchor" the receptor into the membrane, expression of the modified gene will result in the secretion, in soluble form, of only the extracellular ligand-binding domain. Standard ligand-binding assays may then be performed to ascertain the degree of binding of a candidate compound to the extracellular domain so produced. It may of course be necessary, using site-directed mutagenesis, to produce several different versions of the extracellular regions, in order to optimize the degree of ligand binding to the isolated domains.

It will be appreciated that the production of such extracellular ligand binding domains may be accomplished in a variety of host cells. Mammalian cells such as CHO cells may be used for this purpose, the expression typically being driven by an expression promoter capable of high-level expression, for example the CMV (cytomegalovirus) promoter. Alternately, non-mammalian cells, such as insect Sf 9 (Spodoptera frugiperda) cells may be used, with the expression typically being driven by expression promoters of the baculovirus, for example the strong, late polyhedron protein promoter. Filamentous fungal expression systems may also be used to secrete large quantities of such extracellular domains of the GLP-2 receptor. Aspergillus nidulans, for example, with the expression being driven by the alcA promoter, would constitute such an acceptable system. In addition to such expression hosts, it will be further appreciated that any prokaryotic or other eukaryotic expression system capable of expressing heterologous genes or gene fragments, whether intercellularly or extracellularly would be similarly acceptable.

The availability of isolate extracellular ligand-binding domains of the receptor protein makes it feasible to determine the 3-dimensional structures of these ligand-binding regions, with or without a candidate ligand complexed thereto, by a combination of X-ray crytstallographic and advanced 2D-NMR techniques. In this way, additional new candidate compounds, predicted to have the required interactions with the 3-dimensional receptor structure, can be specifically designed and tested.

With large domains, crystallography is the method of choice for structure determination of both the domain in isolation, and of the co-complex with the natural ligand (or an appropriate antagonist or agonist molecule). If a particular domain can be made small enough, for example approximately 100-130 amino acids in length, then the powerful technique of 2-D NMR can also be applied to structure determination. This enables not only the determination of the domain structure, but also provides dynamic information about the drug-receptor interaction.

For use particularly in detecting the presence and/or location, for example in intestinal tissue, the present invention also provides, in another of its aspects, labelled antibody to a GLP-2 receptor. To raise such antibodies, there may be used as immunogen either the intact, soluble receptor or an immunogenic fragment thereof, produced in a microbial or mammalian cell host as described above or by standard peptide synthesis techniques. Regions of the GLP-2 receptor particularly suitable for use as immunogenic fragments include those corresponding in sequence to an extracellular region of the receptor, or a portion of the extracellular region, such as peptides consisting of 10 or more amino acids of the 401-509 region of SEQ ID NO: 2. With regard to the human GLP-2 receptor (SEQ ID NO: 12), peptide comprising the mature extracellular domain (residues 65-180); intracellular loop 3 (resides 363-385) and the intracellular C-terminal domain (residues 442-533) may be usefully employed as immunogens for the production of antibodies to the human GLP-2 receptor.

Antibodies to the desired GLP-2 receptor or fragment immunogen are available, for polyclonal antibody production, from the blood of an animal that has been immunized with the immunogen. Alternatively, for monoclonal antibody production, immunocytes such as splenocytes can be recovered from the immunized animal and fused, using hybridoma technology, to a myeloma cells. The fusion products are then screened by culturing in a selection medium, and cells producing antibody are recovered for continuous growth, and antibody recovery. Recovered antibody can then be coupled covalently to a detectable label, such as a radiolabel, enzyme label, luminescent label or the like, using linker technology established for this purpose.

Animal model systems which elucidate the physiological and behavioral roles of the GLP-2 receptor are produced by creating transgenic animals in which the activity of the GLP-2 receptor is either increased or decreased, or the amino acid sequence of the expressed GLP-2 receptor is altered, by a variety of techniques. Examples of these techniques include, but are not limited to: 1) Insertion of normal or mutant versions of DNA encoding a GLP-2 receptor, by microinjection, electroporation, retroviral transfection or other means well known to those skilled in the art, into appropriate fertilized embryos in order to produce a transgenic animal or 2) Homologous recombination of mutant or normal, human or animal version of these genes with the native gene locus in transgenic animals to alter the regulation of expression or the structure of these GLP-2 receptor sequences. The technique of homologous recombination is well known in the art. It replaces the native gene with the inserted gene and so is useful for producing an animal that cannot express native GLP-2 receptors but does express, for example, an inserted mutant GLP-2 receptor, which has replaced the native GLP-2 receptor in the animal's genome by recombination, resulting in under expression of the transporter. Microinjection adds genes to the genome, but does not remove them, and so is useful for producing an animal which expresses its own and added GLP-2 receptors, resulting in over expression of the GLP-2 receptors.

One means available for producing a transgenic animal, with a mouse as an example, is as follows: Female mice are mated, and the resulting fertilized eggs are dissected out of their oviducts. The eggs are stored in an appropriate medium such as M2 medium. DNA or cDNA encoding a GLP-2 receptor is cesium chloride purified from a vector by methods well known in he art. Inducible promoters may be fused with the coding region of the DNA to provide an experimental means to regulate expression of the transgene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a piper puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only methods for inserting DNA into the egg cell, and is used here only for exemplary purposes.

The invention having been described above, may be better understood by referring to the following examples. The following examples are offered for the purpose of illustrating the invention and should not be interpreted as a limitation of the invention.

EXAMPLE 1

Isolation of the GLP-2 Receptor

PCR-assisted Cloning of Partial Rat and Mouse GLP-2 Receptor cDNAs

Rat Neonate Intestine cDNA library (Stratagene, La Jolla, Calif.; Cat. 936508) and Mouse Jejunum first strand cDNA was prepared. Degenerate primers M-2F/S (SEQ ID NO: 3) and M-7R/S (SEQ ID NO: 4) were used to amplify a partial fragment of the rat GLP-2 receptor from the Rat Neonate Intestine cDNA library and of the mouse GLP-2 receptor from Mouse Jejunum template. The protocol is described below:

Degenerate PCR:
6 µl 10× VENT buffer from New England Biolabs
6 µl 2.5 µM each stock dATP, dCTP, dGTP and dTTP
4 µl rat neonate intestine cDNA (1:10 dilution)
3 µl 25 µM M2F/S primer [5'-TTTTTCTAGAASRTSAT-STACACNGTSGGCTAC-3'] (SEQ ID NO: 3)
3 µl 25 µM M7R/S primer [5'-TTTTCTCGAGCCARCARC-CASSWRTARTTGGC-3'] (SEQ ID NO: 4)
2 µl (10 units) Amplitaq DNA polymerase (Perkin Elmer)
36 µl ddH$_2$O.
Reaction conditions: 35 cycles at 94° C., 2° min.; 94° C., 1 min.; 53° C., 30 sec.; 72° C., 1 min.

The predominant PCR product was a 303 base pair (bp) DNA fragment. 30 µl samples of the above PCR were purified using the QIAGEN PCR purification kit and eluted in 30 µl ddH$_2$O. The resulting product was then re-amplified using the same degenerate PCR conditions, with the exception only of 31 cycles at 94° C.

The predominant product at 303 base pair (bp) was cut out and purified using QIAGEN QIAquick gel purification protocol into 30 µl ddH$_2$O. The resulting product was then reamplified using the same degenerate PCR conditions, with the exception only of 31 cycles at 94° C.

Next, double digest (Xba I and Xho I) was done on the entire reamplified PCR reaction as follows: 28 µl DNA; 16 µl 10× One-Phor-All buffer (Pharmacia); 2 µl (40 units) Xba I enzyme (Pharmacia); 2 µl (40 units) Xho I enzyme (Pharmacia); and 30 µl ddH$_2$O.

The samples were digested 4 hours in 37° C. water block heater, brought up to 100 µl volume with ddH$_2$O (sterile) and purified by (1) equal amount (100 µl) chloroform extraction; (2) weekend precipitation with 2 volumes ethanol/10 volumes 3 M sodium acetate; (3) 1× wash with 70% EtOH; and (4) resuspension in 10 µl 1× TE (pH 8.0).

pBluescript clone 5HT1F#9 was next digested with Xba I and Xho I as follows:
10 µl DNA (pBluescript clone 5HT1F#9)
5 µl 10× NEBuffer 2 (New England Biolabs)
3 µl (1:20 dilution=3 units) Xba I (New England Biolabs)
3 µl (1:20 dilution=3 units) Xho I (New England Biolabs)
5 µl (10×) BSA (New England Biolabs)
24 µl ddH$_2$O.

The sample was digested for 3 hours in 37 C water block heater, heat-inactivated at 65° C. for 20 min and purified using GeneCleanII kit from BIO 101. Aliquots of the PCR reactions were cloned into the above pBluescript plasmid vector using T4 DNA ligase kit (New England Biolabs) and transformed into Epicurean Coli XL-2 Blue MRF' Ultracompetent cells (Stratagene). The transformation was plated onto 2×YT+ AMP plates and single colonies were picked. DNA minipreps were made using QIAGEN QIA-prep 8 miniprep kit and the sequences of the fragments were determined using ABI system. Novel sequences were identified containing a partial fragment of the rat and mouse GLP-2 receptor sequence.

Cloning of cDNA with complete GLP-2 receptor coding region was achieved as follows: First, cDNA libraries from the following three tissues were used for screening,
1. Rat Hypothalamus (RHT)
2. Rat Hind Brain (RHB)
3. Rat Duodenum and Jejunum (RDJ)

The three cDNA libraries were prepared by priming with random primer and subcloning unidirectionally into Hind III and Not I sites of pcDNA3.

Next, the three cDNA libraries were homology screened by a degenerate oligo C4-4 [5'-AACTACATCCACMKG-MAYCTGTTYVYGTCBTTCATSCT-3'] (SEQ ID NO: 5) by colony lifts and filter hybridization. The following hybridization conditions were employed: 5× SSPE (1× SSPE is 0.18 M NaCl, 10 mM NaH$_2$PO$_4$ (pH 7.4), 10 mM EDTA (pH 7.4)) and 5× Denharts solution (1% Ficoll, 1% Polyvinylpyrrolidone, 1% BSA); 25 mg/ml salmon sperm DNA.

Filters were hybridized at 50° C. overnight. Then the filters were washed 2 times in 2× SSPE and 1% SDS at room temperature for 30 min, 2 times in 2× SSPE and 1% SDS at 50° C. for 20 min per wash, and finally two times in 1× SSPE and 0.5% SDS. Positive clones were identified by autoradiograhpy. A plug of 1 cm$^2$ surrounding the positive clone was removed from the plate and placed in 1 ml of 2× YT+20% Glycerol, vortexed and was frozen at –80° C.

Plasmid DNA from positive plugs was prepared as follows: 100 ml of bacterial culture of each positive plug was grown on an agar plate. The bacterial cells were scraped and resuspended in 1 ml of 2× YT medium+20% Glycerol. Bacterial pellet from the 250 ml of bacterial resuspension was resuspended in 150 ml of Solution I (50 mM Glucose, 10 mM Tris-HCl, 1 mM EDTA), lyse in Solution II (0.2 M NAOH, 1% SDS), neutralized with ice cold Solution III (Potassium acetate; 4 vol. of 5 M potassium acetate+1 vol. of 10 M acetic acid). After pelleting bacterial DNA, 340 ml isopropanol was added to the supernatant. This was centrifuged at max for 15 min. The pellet was resuspended in TE+20 mg/ml RNase, incubated at 37 C for 30 minutes and precipitated with isopropanol+0.2 M potassium acetate. After centrifugation, the pellet was washed with 70% alcohol, allowed to air dry and resuspended in TE.

Plasmid DNA from 2777-clone pools of rat hypothalamus cDNA library RHT cDNA library was next exploited as follows: Two primers were designed from an area of the PCR-cloned GLP-2 receptor cDNA sequence that did not have identity to known receptors of the gene family. The two primers P23-R1 and P23-F1 amplified a 196 bp fragment only from novel clone DNA but not with GLP-1 receptor cDNA or PACAP receptor cDNA. The Expand™ PCR system from Boehringer Mannheim (Cat. 1681-842) was used under the following conditions:
2 µl of 10× Expand™ Buffer 1
2.8 µl of 2.5 mM dNTP mix
0.6 µl of primer P23-R1 [5'-TCATCTCCCTCTTCTTG-GCTCTTAC-3'] (SEQ ID NO: 6)
0.6 µl of primer P23-F1 [5'-TCTGACAGATATGACATC-CATCCAC-3'] (SEQ ID NO: 7)

0.3 µl of Expand PCR enzyme (1 unit)
12.7 µl water
1 µl DNA
Reaction conditions: 32 cycles at 93° C., 40 sec; (cycles) 58° C., 40 sec; (cycles) 68° C., 40 sec.

DNAs from each positive plug or pool of 2777-clone pools were amplified with specific primers P23-F1 and P23-R1 under the conditions specified above. Out of 1057 C4-4 hybridization-positive plugs and 884 2777-clone pools only five template sources amplified a 196 bp PCR product. These were: (1) Plug 334, (2) Plug 780, (3) RHT pool 233, (4) RHT pool 440, and (5) RHT pool 587.

Amplification of GLP-2R cDNA from the five positive templates was then performed. By using one specific primer (P23-R1 or P23-F1) and one primer based on pcDNA3 vector (Invitrogen) sequence (830F or 1186R), the GLP-2R cDNA insert was directly 23 amplified from clonally impure plugs or 2777-clone pools. The sequences of the vector primers were as follows.
830F: [5'-AACCCACTGCTTAC-3'] (SEQ ID NO: 14)
1186R: [5'-CCCAGAATAGAATGACACC-3'] (SEQ ID NO: 15)

The PCR was done, under the following conditions just noted, using Expand™ PCR system.

The most prominent band was reamplified, purified and sequenced. Based on the amplified sequence obtained, additional primers were designed and new sequencing carried out. In this manner the complete sequence of the GLP-2R cDNA inserts in all five sources of clones were determined. Sequence analysis showed that only pool RHT 440 and pool RHT 587 contain clones with complete coding sequence of GLP-2R and that the two clones were identical (derived from the same cDNA clone).

Because of difficulty in clonally purifying the GLP-2 receptor cDNA clone from the RHT 440 or RHT 587 cDNA library pools, the cDNA was amplified and recloned into pcDNA3. Based on the sequence obtained from RHT 440 and RHT 587, two primers were designed one which primed staring 4 bp upstream of the initiation codon and another which primed starting 8 bp downstream of the stop codon.
WBR-C5: [5'-CAGGGGCCGGTACCTCTCCACTCC-3'] (SEQ ID NO: 16)
WBR-C3: [5'-TTGGGTCCTCGAGTGGCCAAGCTGCG-3'] (SEQ ID NO: 17)

The two primers were used to amplify a DNA fragment of approximately 1525 bp fragment under the following PCR conditions using Expand™ PCR system from Boehringer Mannheim (Catalogue no. 1681-842).
10 µl of 10× Expand™ PCR Buffer 1
14 µl of 2.5 mM dNTP mix
3.0 µl of Primer 1 (10 µM) (WBR-C5)
3.0 µl of Primer 2 (10 µM) (WBR-C3)
1.5 µl of Enzyme (5 units)
63.5 µl water
5 µl DNA
Reaction conditions: 5 cycles (93° C., 1 Min; 72° C., 40 s; 60° C., 45 sec; 68° C., 2 min) and 25 cycles (93° C., 1 min; 72° C., 1 min; 68° C., 2 min).

The amplified product was subcloned into Kpn I and Xho I sites of pcDNA3 vector (Invitrogen). Plasmid DNA was prepared using the method described above.

EXAMPLE 2

Functional Assay

Cos-1 cells were transfected as described in Analytical Biochemistry, 218:460-463(1994) with Rat clone 587 GLP-2 receptor, cloned human GLP-2 receptor (pC3/HuGL2R-2), or cloned residue 85 variant human GLP-2 receptor (pC3.1/HuGL2R-MH4), pcDNA3. Rat GLP-1 (7-36) amide was used as a control peptide. Solutions used were as follows:
RSC in RPMI 1640 (49 ml RPMI+1 ml FCS+50 µl chloroquine, 100 mM);
DEAE/RSC Solution: 18.4 ml RCS+1.6 ml DEAE/Dextran (10 mg/ml).

The assay procedure entailed the following:
a) 50 mg of either rat clone 587 GLP-2 receptor, or cloned human GLP-2 receptor, or cloned residue 85 variant human GLP-2 receptor was added (as plasmid pcDNA3) to a 50 ml tube containing six mls. of RSC and incubated at 37° C.
b) Six ml of DEAE/RSC solution was added to each tube and incubated at 37° C. for 2 min.
c) 1.5 ml of COS-1 cell suspension (5.5 millions cells) was added to each tube and incubated for 1 hr 45 min at 37° C.
d) Following incubation, the sample was spun for 5 minutes at low speed, washed with DMEM/F12+10% FBS twice, and the pellet resuspended in 12.5 ml DMEM/F12+10% FBS media.
e) One ml of cell suspension (step d) was added to each well of 6 well plates coated with poly-D-lysine (from Collaborative Biomedical), containing 3 ml of media (0.45 million cells/well).
f) Plates were incubated at 37° C. for 3 days.

Treatment of Transfected Cos-1 cells with GLP-1/GLP-2 analog was done as follows:
Solutions: DMEM/F12 (SFM)+IBMX (3-isobutyl-1-methylxanthin) 0.85 mM+0.1% ascorbic acid and 10 um pargyline (all solutions purchased from Sigma). Media was prepared fresh on day of use.

Assay Procedure: The culture media of each well (transfected 6 well plates, cells) was removed, and the wells were washed once with SFM media. Then 2 ml of SFM+IBMX media was added to each well and plates were incubated at 37° C. for 10 min. Following incubation, the SFM+IBMX was removed from each well and fresh SFM+IBMX media containing GLP-1/GLP-2 (GLP-1,7-36, amide from Sigma, [Gly2]hGLP-2 from Allelix) concentration 1, 3, 10 and 30 nM were added to the appropriate wells. Plates incubated at 37° C. incubated for 30 min. Following incubation, the media were removed from each well. The wells were washed once with 1 ml PBS (Phosphate Buffered Saline). Each well was then treated with 1 ml cold 95% ethanol: 5 mM EDTA (2:1) at 4° C. for 1 hr. Cells from each well then were sraped and transferred into individual eppendorf tubes. Tubes were centrifuged for 5 min at 4° C., and the supernatants were transferred to new eppendorf tubes and dried in speed vacuum. Following drying, tubes were reconstituted in 100 µl of Na-Acetate and kept at 4° C., 25 µl of this solution used for cAMP Assay.

The functional assay was performed as follows: cAMP content for each extract was determined in duplicate by EIA (Enzyme Immuno Assay) using the Amersham Biotrak cAMP EIA Kit (Amersham 225). Results of the assays, illustrated in FIG. 3 and FIG. 8, demonstrate the GLP-2 selectivity exhibited by the cloned rat and human receptors. In a similar functional assay used to users binding to the GLP-1 receptor, the expected specificity for GLP-1 was observed.

EXAMPLE 3

Isolation Of Human GLP-2 Receptor cDNA

Medium-stringency Hybridization Screening of a Human Hypothalamus cDNA Library

One million clones from a λgt10 cDNA library from human hypothalamus (Clontech; Cat. No. 1172a) were screened by plaque lifts on nitrocelluose filters (Amersham; Cat.RPN137E). The probe was prepared by random primer labelling of a DNA fragment containing the complete coding region of rat GLP-2 receptor. The DNA fragment was isolated from clone 587-C1, which contains the complete coding region from SEQ ID NO: 2.

Pre-hybridization and hybridization were each carried out overnight in a hybridization solution consisting of 50% formamide, 5× SSPE, 5× Denhart's solution, 0.5% SDS and salmon sperm DNA (200 mg/ml). After hybridization the filters were washed under the following conditions (medium stringency):

two times at room temperature in 2× SSPE and 0.01% SDS.
two times at 42° C. in 2× SSPE and 0.01% SDS.
two times at 42° C. in 0.2× SSPE and 0.01% SDS.

The filters were autoradiographed and agar plugs, each containing numerous bacteriophage plaques, were picked from regions on the plates corresponding to positive signals on the filter. From one million cDNA clones sampled in the first round screen, there were identified two positive clones (HHP6-1 and HHP13). On secondary screening only HHP13 turned out positive. Several positive plaques (HHS13) from the HHP13 plate were pooled and taken for tertiary screening. Three single positive plaques from this round of screening were picked (HHT13-1, HHT13-2, HHT13-3).

PCR amplification was then used for partial sequencing of the positive clones. On a lawn of bacterial cells (*E. coli* C600Hfl), 10 µl of phage suspension from each clone was applied at marked spots. After 5 hr incubation at 37° C., the phage plaques were clearly visible and covered ~1 cm². A portion of each plaque was transferred to 200 µl of water. The samples were incubated in a boiling water bath for 5 min and centrifuged at room temperature for 10 min. On millilitre of sample was used for PCR amplification with two sets of degenerate primers:

M2FS[5'-TTTTTCTAGAASRTSATSTACACNGTSG-
    GCTAC-3'] (SEQ ID NO: 3) and
M7RS[5'-TTTTCTCGAGCCARCARCCASSWRTART-
    TGGC-3'] (SEQ ID NO: 4); or
C4-4    [5'-AACTACATCCACMKGMNAYCTGT-
    TYVYGTCBTTCATSCT-3'] (SEQ ID NO: 5) and
C9-2R  [5'-TCYRNCTGSACCTCMYYRTTGASRAAR-
    CAGTA-3'] (SEQ ID NO: 8).

The Expand™ PCR system from Boehringer Mannheim (Cat. 1681-842) was used under the following conditions:
5 µl of 10× Expand™ Buffer 3
7 µl of 2.5 mM dNTP mix
1.5 µl of primer M2FS or C4-4
1.5 µl of primer M7RS (with M2FS) or C9-2R (with C4-4)
0.75 µl of Expand PCR enzyme (1 unit)
33.25 µl water and
1 µl DNA.
Reaction conditions were: 32 cycles at 93° C., 1 min; cycles 50° C., 1 min; cycles 45° C., 1 min; cycles 68° C., 2 min.

M2F/S and M7R/S amplified a DNA fragment of about 300 bp and C4-4 and C92-R amplified a DNA fragment of about 700 bp. The PCR products were purified using the QIAGEN QIAquick PCR purification kit (Cat. 28104) and eluted in 50 µl 10 mM Tris, pH 8.0. Sequence analysis of the products revealed no differences between the templates, as expected from the fact that they represent multiple copies of a single cDNA clone (HHT13).

A number of factors indicate that this clone contains coding sequence of the human GLP-2 receptor. One factor is the degree of sequence similarity. The glucagon receptor cDNA can be used to predict the expected degree of sequence conservation found between rat and human receptors. At the nucleotide level, there is 82.6% identity within the coding regions of the rat and human glucagon receptors. At the amine acid level, there is 80.9% identity and 89.1% amino acid similarity between the glucagon receptors of the two species.

In the case of the human GLP-2 receptor cloned herein, the sequence of the partial human GLP-2 receptor cDNA (HHT13) is highly homologous to rat GLP-2 receptor cDNA at both the nucleotide and amino acid level. SEQ ID NO: 9 shows 87.1% identity with the rat GLP-2 receptor cDNA sequence. The predicted amino acid sequence of this cDNA region has 87.4% identity and 93.2% similarity with the predicted amino acid sequence of the rat GLP-2 receptor. The total predicted length of the rat receptor preprotein is 550 amino acids, suggesting about 44% of the coding region of the human receptor had been identified.

Further evidence supporting this conclusion comes from a comparison of the partial human GLP-2 receptor amino acid sequence with the rat GLP-2 receptor and the 3 next closest family members, shown below:

| Receptor Sequence (amino acid) | Percent Identity with HHT13 | Percent Similarity |
|---|---|---|
| GLP-2 receptor (rat) | 87.4 | 93.2 |
| GLP-1 receptor (rat) | 50.0 | 74.1 |
| Glucagon receptor (rat) | 51.4 | 73.9 |
| GIP receptor (rat) | 50.7 | 70.3 |

These comparisons, together with the benchmark provided by sequence similarities between the rat and human glucagon receptors, provide definitive evidence that the cDNA designated HHT13 represents a fragment of the human counterpart of the rat GLP-2 receptor.

The full amino acid sequence of the human GLP-2 receptor can be obtained by first determining the sequence of the complete cDNA inserts in HHT13-1, HHT13-2 and HHT13-3. By using degenerate primers for PCR amplification and subsequent sequencing, we obtained sequence from only part of each insert. It is possible that these identical clones contain an insert which spans the complete coding sequence of the human GLP-2 receptor preprotein. To determine the complete sequence of the cDNA insert, the clones are grown in large quantity to prepare approximately 20 mg of each equivalent clone. The complet cDNA insert is excised by restriction with Eco RI, and subcloned into pcDNA3 (Invitrogen). Alternatively, two primers from vector sequence flanking the insert are used to ampify the complete cDNA insert using the Expand™ PCR sytem from Boehringer Mannheim (Cat. 1681-842). The amplified cDNA is cut with appropriate restriction enzymes and is subcloned into pcDNA3 (Invitrogen).

If a complete coding sequence is not present in the HHT13 clones, cDNA libraries are screened for additional clones to complete the coding region of human GLP-2 receptor cDNA. Preferably human cDNA libraries (from Stratagene or Clontech) representing the following tissues are used for screening: Human hypothalamus; Human fetal brain; Human duodenum and jejunum; Human stomach; and Human fetal intestine.

Two PCR primers are designed from the sequence of human GLP-2 receptor cDNA already determined. These primers are designed such that they could not amplify any related gene family members other than the GLP-2 receptor cDNA itself. A dilution of the cDNA library stock is used to make library sub-pools such that 50,000 clones are represented in each pool. PCR is conducted with the GLP-2 receptor-specific primers to diagnose pools containing a GLP-2 receptor cDNA clone, using the Expand™ PCR system from Boehringer Mannheim (Cat. 1681-842) under the following conditions:

2 µl of 10× Expand™ Buffer 1
2.8 µl of 2.5 mM dNTP mix
0.6 µl of primer P1
0.6 µl of primer P2
0.3 µl of Expand PCR enzyme (1 unit)
12.7 µl water
1 µl of library pool containing 50,000 clones
Reaction conditions: 32 cycles at 93° C., 40 sec; 50-58° C., 40 sec; 68° C., 40 sec.

Sequence is then obtained from the complete GLP-2 receptor cDNA insert from a positive pool. By using one specific primer and one primer based on vector sequence close to the cloning site, the GLP-2 receptor cDNA insert is directly amplified from clonally impure clone pools, using the Expand™ PCR system from Boehringer Mannheim (Catalogue no. 1681-842) most suitably under the following conditions:

2 µl of 10× Expand™ Buffer 1
2.8 µl of 2.5 mM dNTP mix
0.6 µl of Primer 1
0.6 µl of Primer 2
0.3 µl of Enzyme (1 unit)
12.7 µl water
1 µl of library pool stock
Reaction conditions: 32 cycles at 93° C., 45 sec; 50° C., 45 sec; 68° C., 1 min.

The reaction is run on a preparative agarose gel, and the most prominent band is purified and sequenced. Based on the amplified sequence obtained, additional primers are designed to obtain sequence and clones of complete coding region and clone the complete cDNA.

5' RACE and 3' RACE are used to obtain complete coding sequence of the human GLP-2 receptor cDNA. Rapid Amplification of cDNA Ends (RACE) is a procedure routinely used for amplification of DNA sequences from first cDNA strand (easily prepared from mRNA) template between a defined internal site and either 3' or the 5' end of the mRNA. Total or mRNA from different human tissues are commercially available from Clontech. The 3' RACE System (Gibco-BRL Life Technologies; Cat. 18373-019) and 5' RACE System (Cat. 18374-058) kits are used. The manuals of these two products provide detailed protocols. In brief, protocols are as described below.

For the 3' RACE procedure, first strand cDNA synthesis is initiated at the poly (A) tail of mRNA using the adapter primer (provided with system) incorporating a unique sequence for universal PCR amplification of the RACE products. After synthesis of the first strand cDNA from this primer, the original mRNA template is destroyed with RNase H. Amplification is then performed using two primers: one is a gene-specific primer (which will be designed from the available partial cDNA sequence of HHT13); the other is the universal amplification primer provided with the kit. The amplified product is subcloned into a plasmid vector for sequencing.

For the 5' RACE System, the first strand cDNA is synthesized from mRNA using a gene-specific primer (which is based on the available partial cDNA sequence of HHT13) and SuperScript II reverse transcriptase. The original mRNA template is removed by treatment with RNase H. Unincorporated dNTPs, primer, and proteins are separated from cDNA using spin cartridge. A homopolymeric dCTP tail is then added to the 3'-end of the first strand cDNA using TdT enzyme and dCTP nucleotides. PCR amplification is performed using two primers: one is a nested, gene-specific primer designed from the available partial DNA sequence of HHT13; and the other is an "anchor primer" provided with the system. Both primers incorporate restriction sites for subcloning into plasmids and subsequent sequencing.

Sub-cloning of HHT13 λgt10 Clones Into pcDNA3, Their Sequencing and Expression

A. Amplification of cDNA Inserts with λgt10 Primers

On a lawn of bacterial cells (*E. coli* C60OHfl), 10 µl of phage resuspension from each clone was placed at marked spots. After 5 hr incubation at 37° C., the phage plaques were clearly visible. The surface of each plaque was transferred to 200 µl of water. The samples were kept in boiling water bath for 5 minutes and centrifuged at room temperature for 10 minutes. 1 µl of sample was used to amplify with a set of λgt10 primers.

GT10-5KXb [5'-GGGTAGTCGGTACCTCTAGAG-CAAGTTCAGCC-3'] (SEQ ID NO: 18)
vs
GT10-3BXh [5'-ATAACAGAGGATCCTCGAGTATTTCT-TCCAG-3'] (SEQ ID NO: 19)

The Expand™ PCR system from Boehringer Mannheim (Cat. 1681-842) was used under the following conditions:

5 µl of 10× Expand™ Buffer 3
7 µl of 2.5 mM dNTP mix
1.5 µl of primer GT10-5KXb
1.5 µl of primer GT10-3BXh
0.75 µl of Expand PCR enzyme (1 unit)
33.25 µl water
1 µl DNA
Reaction conditions: 5 cycles of 93° C.-40 sec; 50° C.- 1 min; 68° C.-2 min and 30 cycles of 93° C.-40 sec; Ramp to 68° C.-1 min; 68° C.-2 min.

An amplified DNA fragment of about 2200 bp long was seen on the agarose gel from all three clones. The PCR product were purified using the QIAGEN's QIAquick PCR purification kit (Cat. no. 28104) and eluted in 50 µl 10 mM Tris, pH 8.0. The templates were sequenced.

B. Subcloning into pcDNA3 Vector

The amplified and purified DNA from the three clones was restricted with Kpn I and Xho I and subcloned into pcDNA3 restricted with similar restriction enzymes. The plasmids were named pHHT13-1, pHHT13-2, and pHHT13-3. Plasmid DNAs were prepared using either crude method (alkaline treatment, bacterial DNA precipitation with 3 M KOAc, isopropanol precipitation followed by RNAse treatment and second round of isopropanol precipitation) or plasmid DNA kits from Qiagen Inc. The templates prepared using Qiagen's kits were sequenced.

C. Functional Assay

Transfections were carried out with each clone, using the rat GLP-2R, 587 clone as a positive control for cAMP response to GLP-2 peptide. Methods for transfection, cell culture and cAMP assay were identical to those described for the functional assay of rat, 587 clone. Results showed that although the positive control gave good cAMP response in COS cells, none of the HHT13 clones gave any cAMP response. As confirmed by sequencing which showed a frame-shift mutation, the functional data suggested that no functional GLP-2R protein was expressed from these cDNA clones.

D. Comparison of DAN Sequence Between Rat GLP-2R and HHT13 Subclones

The comparison showed a 2 bp deletion at a position corresponding to nucleotides 389-390 of the rat GLP-2R cDNA, resulting in the loss of nucleotides 374-375 of the human GLP-2R cDNA sequence presented herein.

PCR was used to incorporate two bp of the rat GLP-2R DNA sequence into HHT13-1 DNA at the site of the 2 bp frame-shift deletion identified relative to the rat GLP-2R coding sequence. The following primers were designed from HHT13 DNA sequence to insert two bp:
HWBR/2BPI-475F
[5'-ACAGGCATGTCTGGAAGACTTACTCAAG-
  GAACCTTCTGGCAT-3'] (SEQ ID NO: 20)
HWBR/2BPI-506R
[5'-ATGCCAGAAGGTTCCTTGAGTAAGTCT-
  TCCAGACATGCCTGT-3'] (SEQ ID NO: 21)
HWBR-F7 [5'-TTCCTCTGTGGTACCAAGAGGAATGC-
  3'] (SEQ ID NO: 22)
and HWBR-1910R:
[5'-GGTGGACTCGAGGTACCGATCT-
  CACTCTCTTCCAGAATC-3'] (SEQ ID NO: 23)

PCR 1: One ng of pHHT13-1 DNA was used as template to do two PCRs with primers, HWBR-F7 vs HWBR/2BPI-506R and HWBR/2BPI-475F vs HWBR-1910R. The Expand™ PCR system from Boehringer Mannheim (Cat. 1681-842) was used under the following conditions:
5 µl of 10× Expand™ Buffer 1
7 µl of 2.5 mM dNTP mix
1.5 µl of primer HWBR-F7 or HWBR/2BPI-475F
1.5 µl of primer HWBR/2BPI-506R or HWBR-1910R
0.75 µl of Expand PCR enzyme (1 unit)
33.25 µl water and
1 µl DNA.
Reaction conditions: 10 cycles of 92° C.-40 sec; 48° C.-1 min; 68° C.-3 min and 30 cycles of 92° C.-40 sec; 55° C.-40 sec; 68° C.-2 min.

The primers HWBR-F7 and HWBR/2BPI-506R amplified a DNA fragment of 400 bp and HWBR/2BPI-475F and HWBR-1910R amplified a DNA fragment of approximately 1.4 kb on an agarose gel. The two bands were cut out of the agarose gel and purified with Qiaquick gel extraction kit from Qiagen Inc. (Cat no. 28706) and the DNAs were eluted in 50 µl of 10 mM Tris (pH 8.5).

PCR 2 (Extension without primers): Approximately 75 ng of two amplified product from about PCR 1 were mixed and then recombined without primers by extending under the following conditions:
2 µl of 10× Expand™ Buffer 1
2.8 µl of 2.5 mM dNTP mix
0.3 µl of Expand PCR enzyme (1 unit)
8.9 µl water
6 µl of combined PCR 1 products
Reaction conditions: 15 cycles of 92° C.-1 min; 60° C.-5 min; 68° C.-3 min.

PCR 3: 1 µl of amplified mix from PCR 2 was used as template to amplify with HWBR-F7 and HWBR-1910R primers using the following conditions:
10 µl of 10× Expand™ Buffer 1
14 µl of 2.5 mM dNTP mix
3.0 µl of primer HWBR-F7 or HWBR/2BPI-475F
3.0 µl of primer HWBR/2BPI-506R or HWBR-1910R
1.5 µl of Expand PCR enzyme (1 unit)
67.5 µl water and
1 µl DNA.
Reaction conditions: 30 cycles of 92° C.-1 min; 60° C.-1 min; 68° C.-2 min.

A DNA fragment of approximately 1.7 kb was amplified as seen on an agarose gel. The PCR product was purified using the QIAGEN's QIAquick PCR purification kit (cat. no. 28104) and eluted in 50 µl of 10 mM Tris, pH 8.0. The purified product was restricted with Kpn I and subcloned into Kpn I-restricted pcDNA3.1(–)/Myc-His A (Invitrogen, Cat. no. V855-20). One clone, named pc3.1/HuGL2R/MH6 (pHuMH6), had the 1.7 kb insert in correct orientation as checked by PCR using vector vs. insert primers.

Functional Assay

This hybrid clone was compared to rat GLP-2R using the assay described in Example 2. Results showed that the 2 bp "GA" replacement into the putative deletion site yielded a clone encoding a functional GLP-2R protein, as shown by the cAMP response to GLP-2 treatment.

EXAMPLE 6

Isolation of the Full-Length Human GLP-2 Receptor cDNA

Twenty thousand clones from λgt10 cDNA Library from Human Stomach (Clontech; Cat. HL3017a) were plated on each of 100 agar 150 mm plates. SM buffer (0.1 M NaCl, 10 mM $Mg_2SO_4$, 35 mM Tris, pH-7.5, 0.01% gelatin) was added to each plate to obtain 100 phage lysates each containing 20,000 (20 K) pooled clones. The first fifty 20 K phage lysates (20 K pools) were screened by PCR using two primers designed from HHT13 DNA sequence. The template DNA from each pool was prepared by boiling phage lysate for 10 minutes and centrifuging for 10 minutes.
HWBR-113F    [5'-GTGGAGAGGATTTGTGCAAA-
  CATTTC-3'] (SEQ ID NO: 24)
HWBR-578R    [5'-AGAGACATTTCCAGGAGAAGAAT-
  GAG-3'] (SEQ ID NO: 25)
1 µl of each 20 K pool DNA was diagnosed by PCR with HWBR-113F and HWBR-578R primers using the following conditions:
2 µl of 10× Expand™ Buffer 1
2.8 µl of 2.5 mM dNTP mix
0.6 µl of primer HWBR-113F
0.6 µl of primer HWBR-578R
0.3 µl of Expand PCR enzyme (1 unit)
12.7 µl water
1 µl 20 K pool DNA
Reaction conditions: 35 cycles of 92° C.-40 s.; 60° C.-40 s.; 68° C.-1 min.

A. DNA fragment of approximately 450 bp was seen in amplification of templates from two pools (HST 19 and HST 38).

B. Screening of clones from two positive pools: HST 19 and HST 38. 40,000 clones plated from each of two positive 20 K pool were screened by plaque lifts on nitrocellulose filters (Amersham; Cat.RPN137E). The probe was prepared by random primer labelling a DNA fragment from pHHT13-1.

1. The filters were pre-hybridized and hybridized at 42° C. overnight. Hybridization solution consisted of 50% formamide, 5× SSPE, 5× Denhart's solution, 0.5% SDS and salmon sperm DNA (200 mg/ml).

2. After hybridization the filters were washed under the following conditions:
   two times at room temperature in 2× SSPE and 0.01% SDS;
   two times at 42° C. in 2× SSPE and 0.01% SDS; and
   two times at 50° C. in 0.1× SSPE and 0.01% SDS.

3. The filters were autoradiographed and the regions on the plates matching to positive signals were isolated. One positive clone (HST 38-4-30) was isolated from HST 38 pool. 450 bp DNA fragment was amplified from the positive clone by using primers HWBR-113F and HWBR-578R and sequenced. The sequence clearly showed that the plasmid contain 2 bp (AG) at position 373-374 of HHT13 DNA sequence.

The complete insert of clone HST 38-4-30 was amplified using λgt10 primers as described in Example 1. PCR amplified a DNA fragment of approximately 1.4 kb. The amplified DNA was purified and sequenced.

EXAMPLE 7

Reconstruction of a Clone of Full-Length Functional Human GLP-2R cDNA and Functional Assay A 700 bp fragment obtained by Kpn I and Pvu II restriction digest of the amplified DNA from clone HST 38-4-30, and 1.4 kb DNA fragment from Xho I and Pvu II restricted pHHT13-1 DNA were subcloned into Kpn I and Xho I restricted pcDNA3 in a three-way ligation. The new plasmid construct was called pc3/HuGL2R-2. In this manner the full length sequence of the human GLP-2 receptor was obtained.

Functional Assay

The new clone was compared to the rat GLP-2R clone 587 as described previously above. Results showed that the clone encoded a functional human GLP-2R protein, which led to cAMP production in COS cells in response to GLP-2 treatment (FIG. 8).

EXAMPLE 8

Antibodies Directed to the GLP-2 Receptor

1. Antipeptide Antibodies

Antipeptide antibodies were raised in rabbits against an N-terminal peptide (QTRENTTDIWQDESE) (SEQ ID NO: 26), a C-terminal peptide (SEGDGSETLQKLR) (SEQ ID NO: 27) and extracellular loop 1 (SHNSYSKRPDDESG) (SEQ ID NO: 28) or the rat GLP-2 receptor.

Immunocytochemical analysis of serum produced as above confirmed that serum contained antibodies direct to the GLP-2 receptor which do not cross react with the rat GLP-1 receptor.

2. Antibodies to a GLP-2 Receptor Raised Against a Fusion Protein

Polynucleotide encoding the C-terminal region of rat GLP-2 receptor (amino acids 444-550) was spliced to the C-terminus of glutathione S-transferase (GST) in pGEX-2T and expressed in *E. coli* strain SUREI. Protein was purified using affinity chromatography using the above GLP-2 C-terminal fragment fused to the C-terminus of maltose binding protein. Protease degradation was minimized by using a cocktail or protease inhibitors (Boeringer Mannheim).

Antibodies were raised generally according to the method disclosed in Antibodies: A laboratory manual, Harlow and Lane, Cold Spring Harbor Laboratory, 1988. Briefly, the GLP-2-GST fusion protein was used to raise antibodies in rabbits as follows. Initial injection was with 100 μg of fusion protein in complete Freund's adjuvant at multiple sites, intramuscularly and subcutaneously. Booster injections were made at multiple sites intramuscularly with 100 μg of fusion protein in incomplete Freund's adjuvant at days 14, 21, 42 and 56.

Antisera was affinity purified using a GLP-2-MBP fusion protein affinity column. Immunocytochemical analysis confirmed that these antibodies specifically recognize the GLP-2 receptor.

EQUIVALENTS

The foregoing written specification is considered to be sufficient to enable one skilled in the art to practice the invention. Indeed, various modifications of the above-described makes for carrying out the invention which are obvious to those skilled in the field of biochemistry, molecular biology or related fields are intended to be within the scope of the following claims.

We claim:

1. An isolated polynucleotide which encodes a GLP-2 receptor selected from:
   (a) a human GLP-2 receptor comprising the amino acid sequence of amino acids 67-553 of SEQ ID NO: 12; and
   (b) a GLP-2 receptor which is at least 95% identical to amino acids 26-553 of SEQ ID NO: 12 and which exhibits the functional characteristic of selectively binding GLP-2.

2. An isolated polynucleotide which encodes a GLP-2 receptor according to claim 1 wherein said GLP-2 receptor is a human GLP-2 receptor comprising the amino acid sequence of amino acids 67-553 of SEQ ID NO: 12.

3. An isolated polynucleotide according to claim 1, comprising nucleotides 320-1780 of SEQ ID NO: 11.

4. An isolated polynucleotide according to claim 1, wherein said polynucleotide encodes a variant of said human GLP-2 receptor, said variant comprising a substitution of Arg85.

5. An isolated polynucleotide according to claim 4, which encodes a Glu85 variant.

6. An isolated polynucleotide according to claim 1, wherein said polynucleotide encodes for the human GLP-2 receptor of amino acids 26-553 of SEQ ID NO: 12.

7. An isolated polynucleotide according to claim 1, wherein said polynucleotide encodes for the human GLP-2 receptor and said polynucleotide encodes for the amino acid sequence which is at least 95% identical to amino acids 26-553 of SEQ ID NO: 12.

8. The polynucleotide of claim 1, further comprising a label.

9. A recombinant polynucleotide comprising a GLP-2 receptor-encoding polynucleotide as defined in claim 1, and expression controlling elements linked operably therewith to drive expression thereof.

10. A cell that has been genetically engineered by the incorporation expressibly therein of a polynucleotide according to claim 1.

11. The cell according to claim 9, which is a mammalian cell.

12. An isolated polynucleotide according to claim 1, wherein said nucleotide sequence has at least 95% sequence identity to nucleotides 320-1780 of SEQ ID NO: 11, wherein said polynucleotide encodes a mammalian GLP-2 receptor that exhibits the functional characteristics of selectively binding GLP-2.

13. A method for identifying GLP-2 receptor ligands comprising:
   (a) incubating a candidate ligand with a cell as defined in claim 11 or with a membrane preparation obtained therefrom, and then
   (b) determining whether binding between the GLP-2 receptor and the candidate ligand has occurred.

14. A method for identifying GLP-2 receptor ligands, comprising the steps of:
   (a) identifying a cell expressing a functional GLP-2 receptor comprising the amino acid sequence of amino acids 67-553 of SEQ ID NO: 12,
   (b) incubating a candidate ligand with the cell that expresses a functional GLP-2 receptor, or with a membrane preparation derived from said cell; and
   (c) determining whether binding between the GLP-2 receptor and the ligand has occurred.

15. A method according to claim 14, wherein the candidate ligand is incubated with a cell that produces a functional GLP-2 receptor, and the determination of whether binding has occurred between the GLP-2 receptor and the candidate ligand is achieved by measuring change in the intracellular cAMP level, wherein an increase in the cAMP level indicating that the candidate ligand is a GLP-2 agonist.

* * * * *